US011647990B2

(12) United States Patent
Padwal et al.

(10) Patent No.: US 11,647,990 B2
(45) Date of Patent: May 16, 2023

(54) IMPLANT ASSESSMENT USING ULTRASOUND AND OPTICAL IMAGING

(71) Applicant: Verathon Inc., Bothell, WA (US)

(72) Inventors: Monali Padwal, Mercer Island, WA (US); Kendall R. Waters, Maple Valley, WA (US); Joon Hwan Choi, Bothell, WA (US); Fuxing Yang, Bothell, WA (US)

(73) Assignee: Verathon Inc., Bothell, WA (US)

( * ) Notice: Subject to any disclaimer, the term of this patent is extended or adjusted under 35 U.S.C. 154(b) by 132 days.

(21) Appl. No.: 16/691,356

(22) Filed: Nov. 21, 2019

(65) Prior Publication Data

US 2020/0178936 A1 Jun. 11, 2020

Related U.S. Application Data

(60) Provisional application No. 62/775,650, filed on Dec. 5, 2018.

(51) Int. Cl.
A61B 8/08 (2006.01)
A61B 8/00 (2006.01)
G06T 7/00 (2017.01)

(52) U.S. Cl.
CPC .......... A61B 8/5207 (2013.01); A61B 8/0825 (2013.01); A61B 8/4209 (2013.01);
(Continued)

(58) Field of Classification Search
CPC ... A61B 8/0825; A61B 5/7264; A61B 8/5261; A61B 8/5207; A61B 8/4209;
(Continued)

(56) References Cited

U.S. PATENT DOCUMENTS 6,909,792 B1  6/2005 Carrott et al.
7,103,205 B2  9/2006 Wang et al.
(Continued)

FOREIGN PATENT DOCUMENTS

WO  WO-2006119243 A2 * 11/2006  ........... A61B 5/0051
WO  WO-2016057960 A1 *  4/2016  ........... G06T 7/0014

OTHER PUBLICATIONS

S. Joo et al., "Computer-Aided Diagnosis of Solid Breast Nodules: Use of an Artificial Neural Network Based on Multiple Sonographic Features," IEEE Transactions on Medical Imaging, vol. 23, No. 10, pp. 1292-1300, Oct. 2004 (Year: 2004).*

(Continued)

Primary Examiner — Joel Lamprecht
Assistant Examiner — Nyrobi Celestine
(74) Attorney, Agent, or Firm — Snyder, Clark, Lesch & Chung, LLP

(57) ABSTRACT

A system may include an ultrasound probe and a controller unit configured to obtain a baseline ultrasound image of a patient's breast area using the ultrasound probe and to obtain a follow-up ultrasound image of the patient's breast area using the ultrasound probe. The controller unit may further be configured to use one or more machine learning models to compare the baseline ultrasound image with the follow-up ultrasound image; detect a change in a morphology or integrity of the patient's breast area based on the comparison of the baseline ultrasound image with the follow-up ultrasound image; and generate a recommendation for a medical intervention based on the detected change.

21 Claims, 30 Drawing Sheets

(52) U.S. Cl.
CPC ............ *G06T 7/0012* (2013.01); *A61B 8/466* (2013.01); *G06T 2207/30068* (2013.01)

(58) Field of Classification Search
CPC ..... A61B 8/466; A61B 5/4312; A61B 8/5246; G06T 2207/30068; G06T 7/0012–0014; G06T 7/0014
See application file for complete search history.

(56) References Cited

U.S. PATENT DOCUMENTS

| | | | |
|---|---|---|---|
| 7,418,119 B2* | 8/2008 | Leichter | G16H 50/20 382/128 |
| 7,556,602 B2 | 7/2009 | Wang et al. | |
| 8,014,576 B2* | 9/2011 | Collins | G06K 9/00 382/128 |
| 9,536,054 B1 | 1/2017 | Podilchuk et al. | |
| 10,650,518 B2* | 5/2020 | Ryu | G16H 50/30 |
| 2003/0212327 A1 | 11/2003 | Wang et al. | |
| 2004/0146191 A1 | 7/2004 | Lu | |
| 2005/0129297 A1* | 6/2005 | Kamath | A61B 5/7264 382/132 |
| 2005/0283076 A1* | 12/2005 | Hangiandreou | A61B 8/485 600/443 |
| 2007/0165920 A1* | 7/2007 | Gering | A61B 5/055 382/128 |
| 2009/0264758 A1 | 10/2009 | Fujita et al. | |
| 2010/0121178 A1* | 5/2010 | Krishnan | G06T 7/0012 600/411 |
| 2011/0144482 A1* | 6/2011 | Sendai | G06T 7/0012 600/425 |
| 2011/0301461 A1 | 12/2011 | Anite | |
| 2012/0256920 A1* | 10/2012 | Marshall | A61B 6/0414 345/420 |
| 2013/0267850 A1 | 10/2013 | Berman | |
| 2014/0094662 A1* | 4/2014 | Van Epps | A61B 5/0053 600/301 |
| 2015/0051489 A1 | 2/2015 | Caluser et al. | |
| 2015/0150502 A1* | 6/2015 | Wu | A61B 5/015 604/22 |
| 2015/0317794 A1 | 11/2015 | Lee et al. | |
| 2016/0093050 A1* | 3/2016 | Kim | G06V 10/20 382/128 |
| 2016/0135688 A1* | 5/2016 | Ebisawa | A61B 5/708 600/407 |
| 2016/0364526 A1* | 12/2016 | Reicher | G06K 9/6227 |
| 2018/0000453 A1 | 1/2018 | Hunter et al. | |
| 2018/0000461 A1* | 1/2018 | Venkataramani | G06T 7/68 |
| 2018/0279985 A1* | 10/2018 | Martinez-Lorenzo | A61B 6/5247 |
| 2019/0150885 A1* | 5/2019 | Durie | A61B 8/0833 |
| 2019/0247013 A1* | 8/2019 | Malik | G06T 7/136 |
| 2020/0111213 A1* | 4/2020 | Chacon | A61F 2/12 |
| 2020/0167928 A1* | 5/2020 | Heindl | G06T 7/0016 |
| 2021/0074411 A1* | 3/2021 | Ha | A61B 6/5217 |

OTHER PUBLICATIONS

Johannes Gossner: Sonography in capsular contracture after breast augmentation: value of established criteria, new techniques and directions for research, J Ultrasound (2017) 20: pp. 87-89.

Hannah Headon et al.: Capsular Contracture after Breast Augmentation: An Update for Clinical Practice, Archives of Plastic Surgery, vol. 42, No. 5, Sep. 2015, pp. 532-543.

PCT International Search Report and Written Opinion issued for the corresponding international application No. PCT/US2019/062684, dated Feb. 17, 2020, 19 pages.

G. Colombo et al. "Prosthetic Breast Implant Rupture: Imaging-Pictorial Essay." Aesth. Plast. Surg. (2011) 35; pp. 891-900.

R. Guo et al. "Ultrasound Imaging Technologies for Breast Cancer Detection and Management: A Review." Ultrasound in Medicine & Biology; Oct. 2017, 34 pages.

* cited by examiner

IMPLANT ASSESSMENT USING ULTRASOUND AND OPTICAL IMAGING

CROSS-REFERENCE TO RELATED APPLICATION

This patent application claims benefit of priority to U.S. Provisional Application No. 62/775,650, entitled "IMPLANT ASSESSMENT USING ULTRASOUND AND OPTICAL IMAGING" and filed on Dec. 5, 2018, which is hereby incorporated herein by reference in its entirety.

BACKGROUND INFORMATION

An ultrasound probe may generate ultrasound signals using a transducer, such as, for example, a piezoelectric transducer or a capacitive transducer, which converts electrical signals into ultrasound energy and which converts ultrasound echoes back into electrical signals. Ultrasound probes are typically used to identify a target organ or other structures in the body and/or determine features associated with the target organ/structure, such as the size of the organ/structure or the volume of fluid in the organ. For example, an ultrasound probe may be used to generate an ultrasound image of a region of interest and the ultrasound image may be processed or analyzed to identify a particular structure in the region of interest. Identifying particular structures in an ultrasound image may present various challenges.

BRIEF DESCRIPTION OF THE DRAWINGS

FIG. 2B is a diagram illustrating a second exemplary ultrasound system according to an implementation described herein;

FIGS. 4A-4C are diagrams of first, second, and third exemplary cameras, respectively, according to implementations described herein;

DETAILED DESCRIPTION OF PREFERRED EMBODIMENTS

The following detailed description refers to the accompanying drawings. The same reference numbers in different drawings identify the same or similar elements.

Hundreds of thousands of breast augmentation surgeries are performed each year after mastectomies, for corrections of congenital defects, or for cosmetic reasons. A breast augmentation surgery may include the placement of a breast implant into a patient's breast. For example, a breast implant may include a saline implant, a silicone implant, a cohesive gel implant (also referred to as a "gummy bear" implant), or a fat transfer implant. A patient may experience complications after breast implant surgery.

One complication that may result from breast implant surgery is a rupture of the implant capsule. A rupture may result in spilling of implant contents, such as, for example, silicone, into surrounding tissue area (referred to as extra-capsular rupture), or the spilling of implant contents from one compartment of the implant into another compartment (referred to as intracapsular rupture). Another complication that may result from breast implant surgery is capsular contracture. While ruptures may occur infrequently, some studies indicate that capsular contracture may occur in as many as 20% of patients.

Figure 1A:
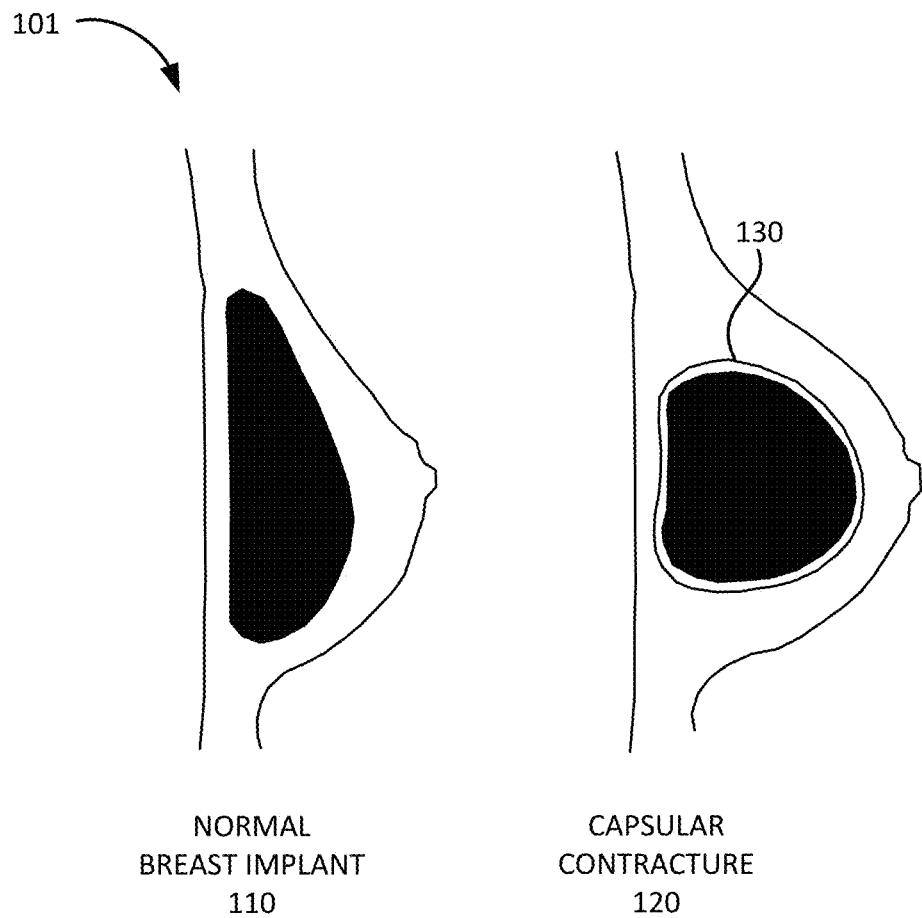
FIGS. 1A and 2B are diagrams comparing a normal breast implant with a breast implant that exhibits capsular contracture according to an implementation described herein.

FIG. 1A is a diagram 101 of side views comparing a normal breast implant 110 to a breast implant with capsular contracture 120. As shown in FIG. 1A, capsular contracture 120 results in contracting the shape of the breast implant, resulting in a deformation of the breast. The capsular contracture may be caused by tissue accumulation 130 at, or near, the implant membrane of the breast implant. Tissue accumulation 130 may result from a thickening of the fibrous capsule that grows around the implant membrane, which may result from excessive fibrotic foreign body reaction to the implant by fibroblasts, macrophages, and lymphocytes. Additionally, or alternatively, a biofilm may form on the implant membrane from bacterial growth, which may cause an exaggerated inflammatory response. The implant membrane, together with the tissue accumulation 130, may be referred to as an implant capsule.

Figure 1B:
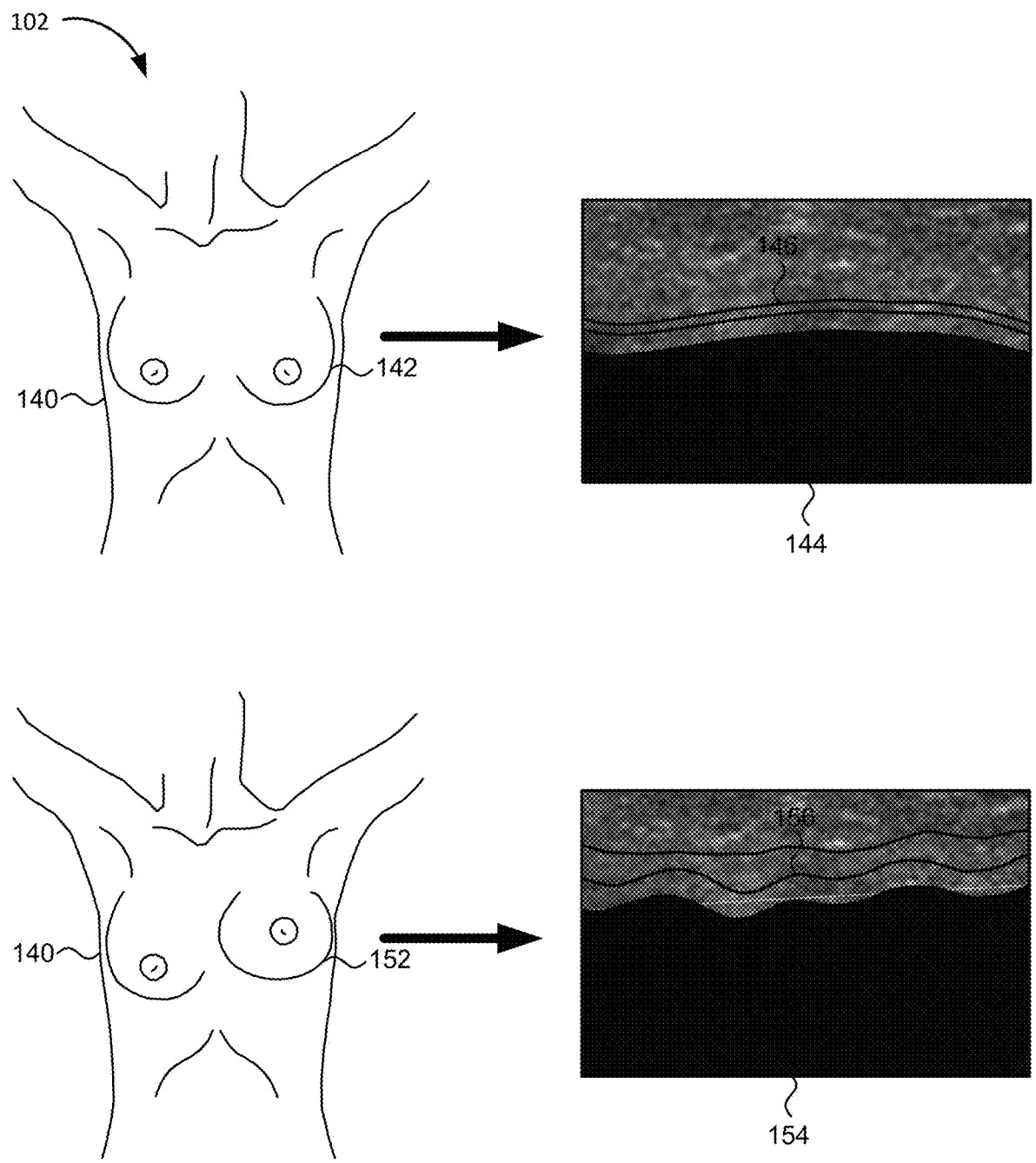
FIG. 1C is a diagram of a table illustrating Baker class values for breast implants according to an implementation described herein.

FIG. 1B is a diagram 102 of frontal views comparing a patient 140 with a normal breast implant during an initial visit to obtain baseline images and with the patient 140 experiencing capsular contracture during a follow-up visit. Patient 140 may have a breast implant 142 with a normal implant capsule during the initial visit, as shown in corresponding B-mode (i.e., 2-dimensional brightness mode) ultrasound image 144 with segmentation performed to identify the boundaries of the implant capsule. Ultrasound image 144 may include an implant capsule 146 that has a normal thickness and does not exhibit radial folds. During the follow-up visit, patient 140 may have a breast implant 152 that has experienced capsular contracture, as shown in corresponding B-mode ultrasound image 154 with segmentation performed to identify the boundaries of the implant capsule. Ultrasound image 154 may include a thickened implant capsule 156. Furthermore, implant capsule 156 may exhibit radial folds due to the capsular contracture, giving implant capsule 156 a wavy appearance.

Furthermore, as shown in FIG. 1B, the capsular contracture of breast implant 152 may cause visible deformation of the breast of patient 140. For example, if the capsular contracture is severe toward the bottom of the breast, breast implant 152 may be pushed upward. Similarly, if the capsular contracture is severe on the medial side of the breast, breast implant 152 may be pushed laterally (not shown in FIG. 1B). Thus, capsular contractures of breast implants may result in implant deformation, a thickening of the implant capsule, and/or an increased number of radial folds in the implant capsule. The deformation may be detected through visual inspection and the thickening of the implant capsule and/or the increased number of radial folds may be detected via ultrasound images of the implant capsule.

Figure 1C:
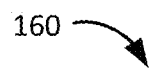

Capsular contractures of breast implants may differ in severity. The severity of capsular contracture may be measured using a Baker class value. FIG. 1C is a diagram of a table 160 illustrating Baker class values for breast implants according to an implementation described herein. As shown in FIG. 1C, table 160 includes a Baker class value column 162, a firmness/pain column 164, an implant palpability column 166, and an implant visibility column 168. Baker class value column 162 identifies a particular Baker class. Firmness/pain column 164 identifies a corresponding firmness and/or pain description associated with the particular Baker class. Implant palpability column 166 identifies a corresponding palpation description associated with the particular Baker class. Implant visibility column 168 identifies a corresponding visibility description associated with the particular Baker class. Thus, a clinical evaluation by a health care provider may help identify a Baker class associated with a patient's breast implant.

The Baker class may be used to select a medical intervention for the patient. For example, Baker class values of 1 and 2 may be recommended for non-surgical options, such as massage, vitamin E supplementations, steroid injections, or drugs, such as leukotriene pathway inhibitors, while Baker class values of 3 and 4 may be recommended for surgical intervention, such as capsulotomy, capsulectomy, autologous fat transfer, or implant replacement. Thus, an accurate determination of the Baker class may be important in selecting the most appropriate medical intervention.

However, the clinical evaluation by itself may not be sufficient to confidently determine the Baker class or determine an appropriate medical intervention. Furthermore, other types of quantitative clinical grading may offer more information about the type of medical intervention that may be appropriate. Therefore, medical imaging may be used in addition to a visual and palpatory assessment by a health care provider. For example, Magnetic Resonance Imaging (MRI) may be recommended to assess the status of the breast implant. However, MRI imaging may be costly and require technical expertise to interpret.

Implementations described herein relate to implant assessment using ultrasound and optical imaging. A system may include a controller unit that includes a user interface and is in communication with an ultrasound probe for capturing ultrasound images and a camera for capturing optical images. The controller unit may be configured to obtain baseline ultrasound images, captured using the ultrasound probe, of a patient's breast area and to obtain baseline optical images, captured using the camera, of the patient's breast area. The controller unit may be further configured to obtain, to a later time, such as during a subsequent patient follow-up visit, follow-up ultrasound images using the ultrasound probe and follow-up optical images using the camera.

The controller unit may be further configured to use one or more machine learning models to compare the baseline ultrasound images with the follow-up ultrasound images and to compare the baseline optical images with the follow-up optical images, to detect a change in a morphology or integrity of the patient's breast area based on the comparisons, and to generate a recommendation for a medical intervention based on the detected change.

In some implementations, the controller unit may be further configured to obtain baseline three-dimensional (3D) scan images of the patient's breast area using a depth camera, to obtain follow-up 3D scan images of the patient's breast area using the depth camera, to use the one or more machine learning models to compare the baseline 3D scan images with the follow-up 3D scan images, and to further detect the change in the morphology or integrity of the patient's breast area based on the comparison of the baseline 3D scan images with the follow-up 3D scan images.

In some implementations, the controller unit may be further configured to obtain baseline elastography images of the patient's breast area using the ultrasound probe, to obtain follow-up elastography images of the patient's breast area using the ultrasound probe, to use the one or more machine learning models to compare the baseline elastography images with the follow-up elastography images, and to further detect a change in the morphology, integrity, and/or stiffness of the patient's breast area based on the comparison of the baseline elastography images with the follow-up elastography images.

In some implementations, the controller unit may be further configured to obtain baseline thermal camera images of the patient's breast area using a thermal camera, to obtain follow-up thermal camera images of the patient's breast area using the thermal camera, to use the one or more machine learning models to compare the baseline thermal camera images with the follow-up thermal camera images, and to further detect a change in the morphology, integrity, and/or temperature variation of the patient's breast area based on the comparison of the baseline thermal camera images with the follow-up thermal camera images.

Thus, in some implementations, the controller unit may be configured to compare only ultrasound images; in other implementations, the controller unit may be configured to compare ultrasound and optical images; in yet other implementations, the controller unit may be configured to compare ultrasound, optical, and 3D scan images; and in yet other implementations, the controller unit may be configured to compare ultrasound, optical, 3D scan, and thermal camera images.

Furthermore, in some implementations, the controller unit may be further configured to use the one or more machine learning models to perform a segmentation of an implant capsule for an implant associated with the patient's breast area. The controller unit may further determine a thickness of the implant capsule and/or determine a radial fold count for the implant capsule. Moreover, in some implementation, the controller unit may further be configured to use the one or more machine learning models to determine whether the patient's breast area is associated with an extracapsular rupture, an intracapsular rupture, capsular contracture, and/or a fluid collection, such as a seroma, abscess, or a hematoma.

In some implementations, a machine learning model may be trained to output a quantitative clinical grading value for the morphology or integrity of the patient's breast area based on the comparisons. The quantitative clinical grading value may include, for example, a Baker class value, an implant capsule thickness value, a radial fold count value, an implant capsule smoothness value, and/or another type of quantitative clinical grading value.

In some implementations, the controller unit may be further configured to obtain a 3D scan image of the patient's breast area using one or more depth cameras, generate a 3D geometrical feature plot using the obtained 3D scan image, and use the generated 3D geometrical feature plot as an input into the one or more machine learning models. The 3D geometrical feature may include, for example, curvature, symmetry, smoothness, distance from a particular location, and/or another type of 3D geometrical feature.

In some implementations, the controller unit may be further configured to use the one or more machine learning models to perform a segmentation of an implant capsule, a rupture area, or a fluid collection in ultrasound images of the patient's breast area and to use a set of ultrasound images that include the segmentation of the implant capsule, the rupture area, or the fluid collection to generate a three-dimensional (3D) shape of the implant capsule, the rupture area, or the fluid collection.

In some implementations, obtaining the ultrasound images may include dividing a breast area into sectors, scanning individual sectors using the ultrasound probe, and indicating, on a user interface, which sectors have been scanned. The user interface may be configured to receive a selection of a scanned sector and to display an ultrasound image associated with the selected scanned sector.

In some implementations, implant assessment may be performed without obtaining baseline images. Thus, implant assessment may be performed using one or more machine learning models on only follow-up images for a patient, without baseline images being available for the patient. The follow-up images may include one or more of ultrasound images, optical images, 3D scan images, and/or thermal camera images of the patient's breast area. For example, the controller unit may be configured to obtain an ultrasound image of a patient's breast area, obtain at least one of an optical image of the patient's breast area, a three-dimensional (3D) scan image of the patient's breast area, or a thermal camera image of the patient's breast area, and use one or more machine learning models to compare the ultrasound image with the at least one of the optical image of the patient's breast area, the 3D scan image of the patient's breast area, or the thermal camera image of the patient's breast area. The controller unit may then detect a change in a morphology or integrity of the patient's breast area based on the comparison and generate a recommendation for a medical intervention based on the detected change. Furthermore, in some implementations, the controller unit may perform particular types of processing without using a machine learning model. For example, the controller unit may generate a 3D geometrical feature plot from one or more 3D scan images without using a machine learning model.

A machine learning model may include a computer program trained using a training set of images, and/or other types of input, to identify a particular feature in an image, and/or to classify the image, or an identified feature in the image, into a particular class from a set of classes. In some implementations, a machine learning model may include a deep learning artificial neural network (DNN), such as a convolutional neural network (CNN). A CNN may be trained to develop multiple convolution matrices, also known as kernels, to identify features in ultrasound images, and/or optical images, including, for example, intensity transitions, shapes, texture information, etc., to identify a particular tissue structure and/or pathology in an image.

A CNN may include multiple layers of nodes, including an input layer, one or more convolution layers, one or more output computing layers, one or more pooling layers, and an output layer. A convolution layer may perform a convolution operation on the output of a set of nodes in the input layer associated with pixels within an area defined by the receptive field of the convolution layer. A pooling layer reduces a set of outputs from adjacent nodes in a convolution layer to reduce the dimensionality of a feature map generated by the convolutional layer. An output computing layer may generate an output for each node in a pooling layer based on an output function, such as, for example, a based on a rectifier activation function. The output layer may include a fully connected layer that generates an output that identifies a feature of interest and/or that classifies an input into a particular class from a set of classes.

A CNN may be trained using supervised learning, in which a set of images that has been labeled to identify a feature of interest and/or classified in a particular class from a set of classes. For example, to train a CNN to perform segmentation to identify an implant capsule, a set of ultrasound images in which the implant capsule has been labeled may be used to train the CNN.

In other implementations, a different type of machine learning model may be used, such as, for example, a linear classifier, a naive Bayesian classifier, a kernel density estimation classifier, a decision tree classifier, a support vector machine classifier, a maximum entropy classifier, and/or another type of classifier. Furthermore, in other implementations, a machine learning model may be trained using unsupervised learning, in which input images have not been labeled with a predetermined classification.

Although implementations described herein refer to scanning a breast area, in other implementations, other body areas, organs, joints, and/or vessels may be scanned. For example, implementations described herein may be used to assess the morphology and/or integrity of an implant in another part of a patient's body, such as a gluteal muscle implant, a calf muscle implant, a pectoral muscle implant, a deltoid muscle implant, and/or another type of implant.

Figure 2A:
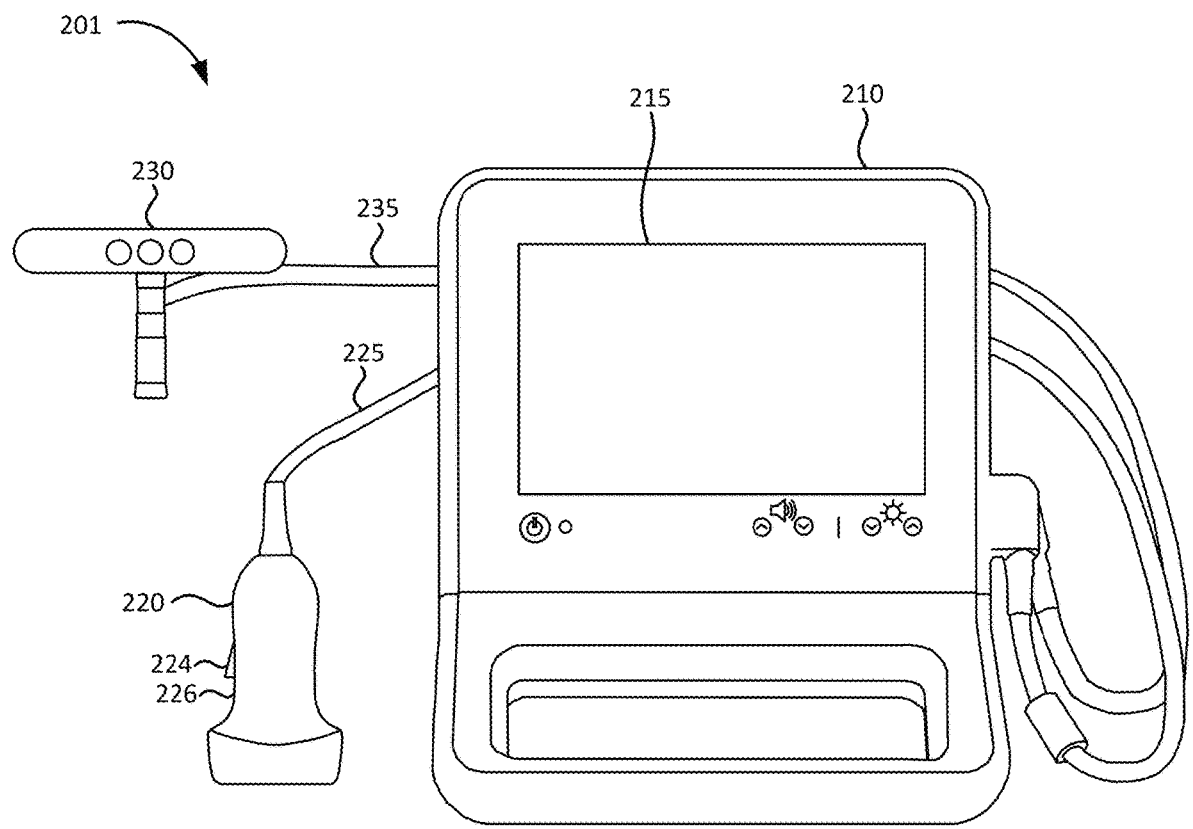
FIG. 2A is a diagram illustrating a first exemplary ultrasound system according to an implementation described herein.

FIG. 2A is a diagram illustrating an exemplary system 201 according to an implementation described herein. As shown in FIG. 2A, system 201 may include a controller unit 210, an ultrasound unit 220, an ultrasound probe cable 225, a depth camera 230, and a depth camera cable 235.

Controller unit 210 may house and include one or more processors and/or processing logic configured to process reflected ultrasound energy that is received by ultrasound probe 220 to produce ultrasound images of a scanned anatomical region and to process optical images captured by depth camera 230. Furthermore, controller unit 210 may include display 215 to enable a user to control the operation of ultrasound probe 220 during an ultrasound scan and/or depth camera 230 while capturing optical images, monitor the progress of an ultrasound scan, view ultrasound images from a scan, view optical images captured by depth camera 230, activate a machine learning model to detect a change in a morphology or integrity of the patient's breast area based on obtained ultrasound images and/or optical images, and/or generate a recommendation for a medical intervention based on the changes detected by the machine learning model. For example, display 215 may include an output display/screen, such as a liquid crystal display (LCD), light emitting diode (LED) based display, touchscreen, and/or another type of display that provides text and/or image data to a user.

Furthermore, display 215 may provide instructions for positioning ultrasound probe 220 relative to a selected anatomical portion of a patient. Alternatively, ultrasound probe 220 may include a small display (not shown in FIG. 2A) that provides instructions for positioning ultrasound probe 220. Display 215 may also display two-dimensional or three-dimensional images of the selected anatomical region. In some implementations, display 215 may include a graphical user interface (GUI) that allows the user to select various features associated with an ultrasound scan. For example, display 215 may include selection items (e.g., buttons, dropdown menu items, checkboxes, etc.) to select an aiming mode for ultrasound probe 220 and/or to initiate a 3D scan after ultrasound probe 220 has been successfully positioned with respect to a patient's area of interest. Furthermore, display 215 may include selection items to select particular types of ultrasound images to be obtained, such as B-mode images, probability mode (P-mode) images, Doppler mode ultrasound images (e.g., Power Doppler, Continuous Wave Doppler, Pulsed Wave Doppler, etc.), harmonic mode ultrasound images, motion mode (M-mode) ultrasound images, and/or any other type of imaging modality that uses ultrasound data. A P-mode ultrasound image may correspond to an ultrasound image (e.g., a B-mode ultrasound image, etc.) in which each particular pixel is mapped to a probability indicating whether that particular pixel is within or part of a target organ/structure.

Ultrasound probe 220 may house one or more ultrasound transducers configured to generate ultrasound energy at a particular frequency and/or pulse repetition rate and to receive reflected ultrasound energy (e.g., ultrasound echoes) and convert the reflected ultrasound energy into electrical signals. For example, in some implementations, ultrasound probe 220 may be configured to transmit ultrasound signals in a range that extends from approximately about two megahertz (MHz) to approximately 10 or more MHz (e.g., 18 MHz). In other implementations, ultrasound probe 220 may be configured to transmit ultrasound signals in a different range. Furthermore, ultrasound probe 220 may house one or more motors for controlling the movement of the ultrasound transducer.

Moreover, ultrasound probe 220 may be used to obtain elastography ultrasound images. To capture an elastography ultrasound image, also referred to as acoustic radiation force impulse imaging (ARFI), ultrasound probe 220 may generate a focused ultrasound beam to apply pressure to a patient's tissue via an acoustic radiation force. The extent to which the tissue is displaced along the axis of the beam may indicate tissue stiffness. An elastography ultrasound image may display the measured tissue stiffness at each pixel in the ultrasound image. Additionally, or alternatively, ultrasound probe 220 may be used to obtain shear-wave elasticity imaging (SWEI) elastography ultrasound images, in which shear waves caused by the acoustic radiation force are measured.

Ultrasound probe 220 may include a trigger 224 and a handle 226. A user (e.g., a medical practitioner, etc.) may hold ultrasound probe 220 via handle 226 and press trigger 224 to activate one or more ultrasound transceivers to transmit ultrasound signals toward a patient's area of interest (e.g., a breast area, a particular body organ, a body joint, a blood vessel, etc.). To scan an area of interest, ultrasound probe 220 may be positioned against a surface portion of a patient that is proximate to the anatomical portion to be scanned. The user may apply acoustic gel, or gel pads, to the skin of the patient over the area of interest to provide an acoustical impedance match when ultrasound probe 220 is placed against the skin. The user may then activate a 3D scan of the area of interest by pressing trigger 124, by pressing a scan button on display 215, by speaking a voice command, and/or using another type of scan activation technique. Ultrasound probe 220 may then transmit ultrasound signals through the area of interest and may receive reflected ultrasound signals. The reflected ultrasound signals may be processed into images that are displayed on display 215 and/or stored by controller unit 210.

Activation of trigger 224 initiates an ultrasound scan of a selected anatomical portion while ultrasound probe 220 is in contact with a surface portion of a patient's body when the patient's area of interest is scanned. Ultrasound probe 220 may communicate with controller unit 210 via a wired connection, such as via cable 225. In other implementations, ultrasound probe 220 may communicate with controller unit 210 via a wireless connection (e.g., Bluetooth®, WiFi, etc.).

Depth camera 230 may be configured to capture optical images that include depth information. For example, for each pixel, depth camera 230 may obtain color information (e.g., RGB values) and a depth value. Thus, depth camera 230 may be configured to obtain optical images that include RGB information for each pixel, 3D scan images that include depth information for each pixel, and/or a combined optical and 3D scan image that includes RBG-D information for each pixel. Depth camera 230 may communicate with controller unit 210 via a wired connection, such as via cable 235. In other implementations, depth camera 230 may communicate with controller unit 210 via a wireless connection (e.g., Bluetooth, WiFi, etc.).

Figure 2B:
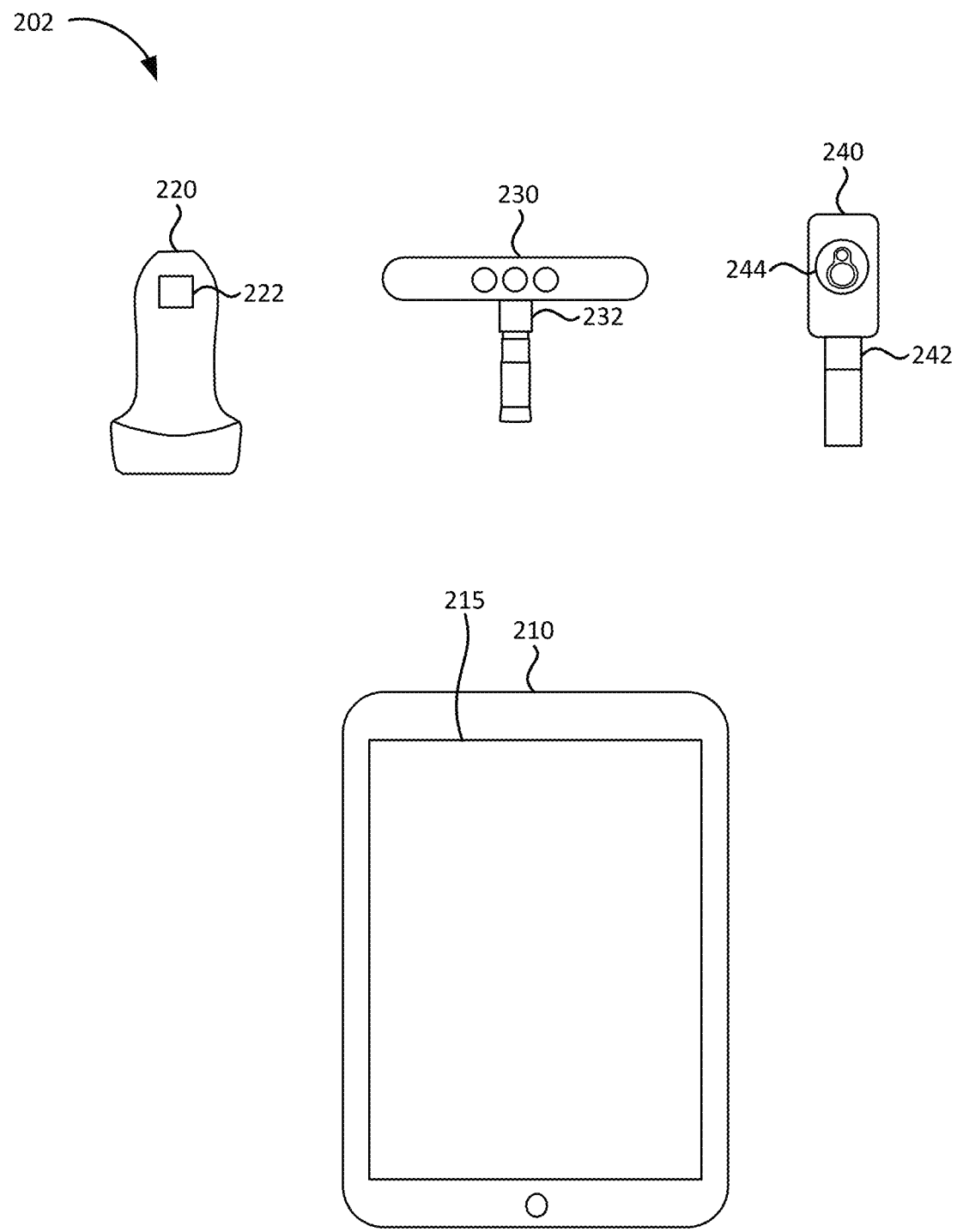

FIG. 2B is a diagram illustrating an exemplary system 202 according to another implementation described herein. As shown in FIG. 2B, system 202 may include controller unit 210, ultrasound probe 220, depth camera 230, and a thermal camera 240. In system 202, controller unit 210 may be implemented in a tablet computer device and ultrasound unit 220 and depth camera 230 may communicate with controller unit 210 using short-range wireless signals, such as, for example, Bluetooth®, WiFi, ZigBee, and/or another short-range wireless communication standard.

Thermal camera 240 may include a handle 242 and a set of thermal sensors 244. Thermal camera 240 may be configured to capture thermal camera images of a patient's breast area. For example, thermal sensors 244 may capture infrared (IR) radiation emitted by, and/or reflected from, the patient and generate a thermographic image that indicates the intensity of the emitted/reflected IR radiation at each pixel in the image.

Ultrasound probe 220 may include a tracking device 222, depth camera 230 may include a tracking device 232, and thermal camera 240 may include a tracking device 242. Tracking devices 222, 232, and 242 may include, for example, a gyroscope, an electromagnetic tracker, an IR tracker, an optical tracker, and/or another type of tracker, which may be used to keep track of the position of ultrasound probe 220, depth camera 230, and thermal camera 240. Keeping track of the position of ultrasound probe 220, depth camera 230, and/or thermal camera 240 while scanning a patient's breast area may facilitate covering or providing ultrasound signals over the whole breast area to generate a 3D scan. For example, a user may be guided by controller unit 210 to move ultrasound probe 220, depth camera 230, and/or thermal camera 240 in particular directions, to hold ultrasound probe 220, depth camera 230, and/or thermal camera 240 at particular angles and/or particular distances away from the patient's breast area, and/or to otherwise adjust ultrasound probe 220, depth camera 230, and/or thermal camera 240 during a scan.

Although FIGS. 2A and 2B show exemplary components of systems 201 and 202, in other implementations, systems 201 and 202 may include fewer components, different components, additional components, or differently arranged components than depicted in FIGS. 2A and 2B. Additionally or alternatively, one or more components of systems 201 or 202 may perform one or more tasks described as being performed by one or more other components of systems 201 and 202.

As an example, thermal camera 240 may also be included in system 201. As another example, in other embodiments, ultrasound probe 220 and/or depth camera 230 may each correspond to a self-contained device that includes a microprocessor housed within ultrasound probe 220, configured to operably control the one or more ultrasound transducers, and to process the reflected ultrasound energy to generate ultrasound images. Accordingly, a display on ultrasound probe 220 may be used to display the generated images and/or to view other information associated with the operation of ultrasound probe 220. In yet other implementations, ultrasound probe 220 and/or depth camera 230 may be coupled to a general-purpose computer, such as a laptop and/or a desktop computer (via a wired or wireless connection) that includes software that at least partially controls the operation of ultrasound probe 220, depth camera 230, and/or thermal camera 240 that includes software to process image information received from ultrasound probe 220, depth camera 230, and/or thermal camera 240.

As another example, while FIGS. 2A and 2B depict ultrasound probe 220 as a hand-held device, in other implementations, ultrasound probe 220 may not correspond to a hand-held device. In some implementations, ultrasound probe 220 may be mounted to a motor assembly on an articulating arm. A patient may lie down on a table in a supine position and the articulating arm may be lowered on the patient's breast area, whereupon the motor assembly may move ultrasound probe 220 to scan different sections of the patient's breast area. In other implementations, ultrasound probe 220 may be mounted to a motor assembly in a recession of a table and a patient may lie down in a prone position with the breast area positioned in the recession, whereupon the motor assembly may move ultrasound probe 220 to scan the patient's breast area.

Figure 3A:
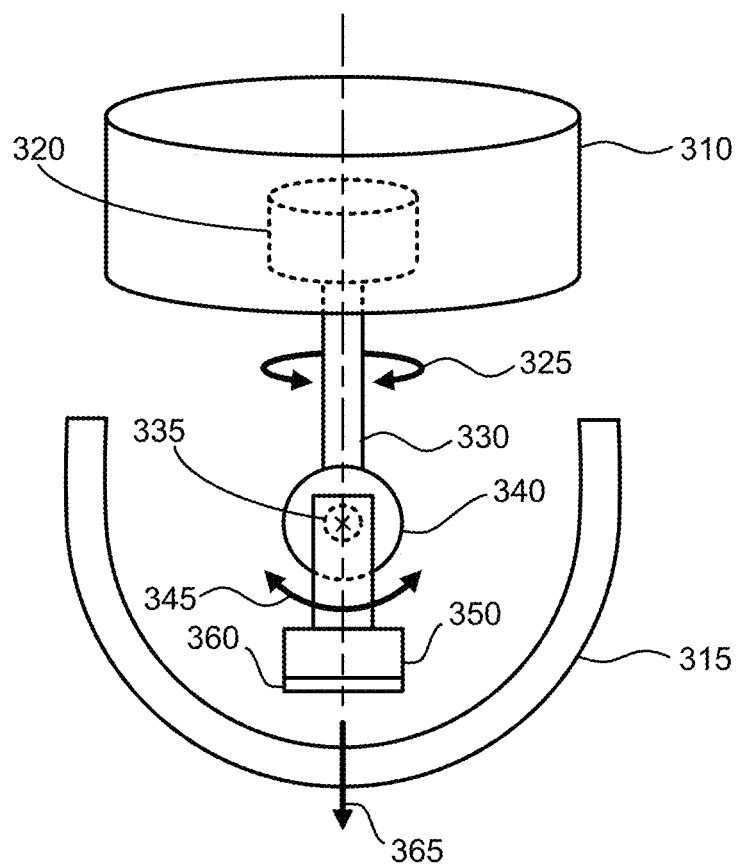
FIGS. 3A-3D are diagrams of first, second, third, and fourth exemplary ultrasound probes, respectively, according to implementations described herein.

FIG. 3A is a diagram of a first exemplary implementation of ultrasound probe 220 according to an implementation described herein. As shown in FIG. 3A, ultrasound probe 220 may include a single transducer element coupled to two rotational motors. In this implementation, ultrasound probe 220 may include a base 310 connected to a dome 315, a theta motor 320, a spindle 330, a phi motor 340, and a transducer bucket 350 with a transducer 360. Theta motor 320, phi motor 340, and/or transducer 360 may include wired or wireless electrical connections that electrically connect theta motor 320, phi motor 340, and/or transducer 360 to controller unit 210.

Dome 315 may enclose transducer bucket 350 and may be formed from a material that provides an appropriate acoustical impedance match to the anatomical portion and/or permits ultrasound energy to be properly focused as it is projected into the anatomical portion. Base 310 may house theta motor 320 and provide structural support to ultrasound probe 220. Base 310 may connect to dome 315 and may form a seal with dome 315 to protect the components of ultrasound probe 220 from the external environment. Theta motor 220 may rotate spindle 330 with respect to base 310 in a longitudinal direction with respect to transducer 360, by rotating around a vertical axis referred to herein as a theta ($\theta$) rotational plane 325. Spindle 330 may terminate in a shaft 335 and phi motor 340 may be mounted onto shaft 335. Phi motor 340 may rotate around an axis orthogonal to the theta rotational plane 325 around a horizontal axis referred to herein as a phi ($\phi$) rotational plane 345. Transducer bucket 350 may be mounted to phi motor 340 and may move with phi motor 340.

Transducer 360 may be mounted to transducer bucket 350. Transducer 360 may include a piezoelectric transducer, a capacitive transducer, and/or another type of ultrasound transducer. Transducer 360, along with transceiver circuitry associated with transducer 360, may convert electrical signals to ultrasound signals at a particular ultrasound frequency or range of ultrasound frequencies, may receive reflected ultrasound signals (e.g., echoes, etc.), and may convert the received ultrasound signals to electrical signals. Transducer 360 may transmit and receive ultrasound signals in a signal direction 365 that is substantially perpendicular to the surface of transducer 360.

Signal direction 365 may be controlled by the movement of phi motor 340 and the orientation of phi motor may be controlled by theta motor 320. For example, phi motor 340 may rotate back and forth across an angle that is less than 180 degrees to generate ultrasound image data for a particular plane and theta motor 320 may rotate to particular positions to obtain ultrasound image data for different planes.

In a 3D scan mode, theta motor 320 may cycle through a set of planes one or more times to obtain a full 3D scan of an area of interest. In each particular plane of the set of planes, phi motor 340 may rotate to obtain ultrasound image data for the particular plane. The movement of theta motor 320 and phi motor 340 may be interlaced in the 3D scan motor. For example, the movement of phi motor 340 in a first direction may be followed by a movement of theta motor 320 from a first plane to a second plane, followed by the movement of phi motor 340 in a second direction opposite to the first direction, followed by movement of theta motor 320 from the second plane to a third plane, etc. Such interlaced movement may enable ultrasound probe 220 to obtain smooth continuous volume scanning as well as improving the rate at which the scan data is obtained.

Figure 3B:
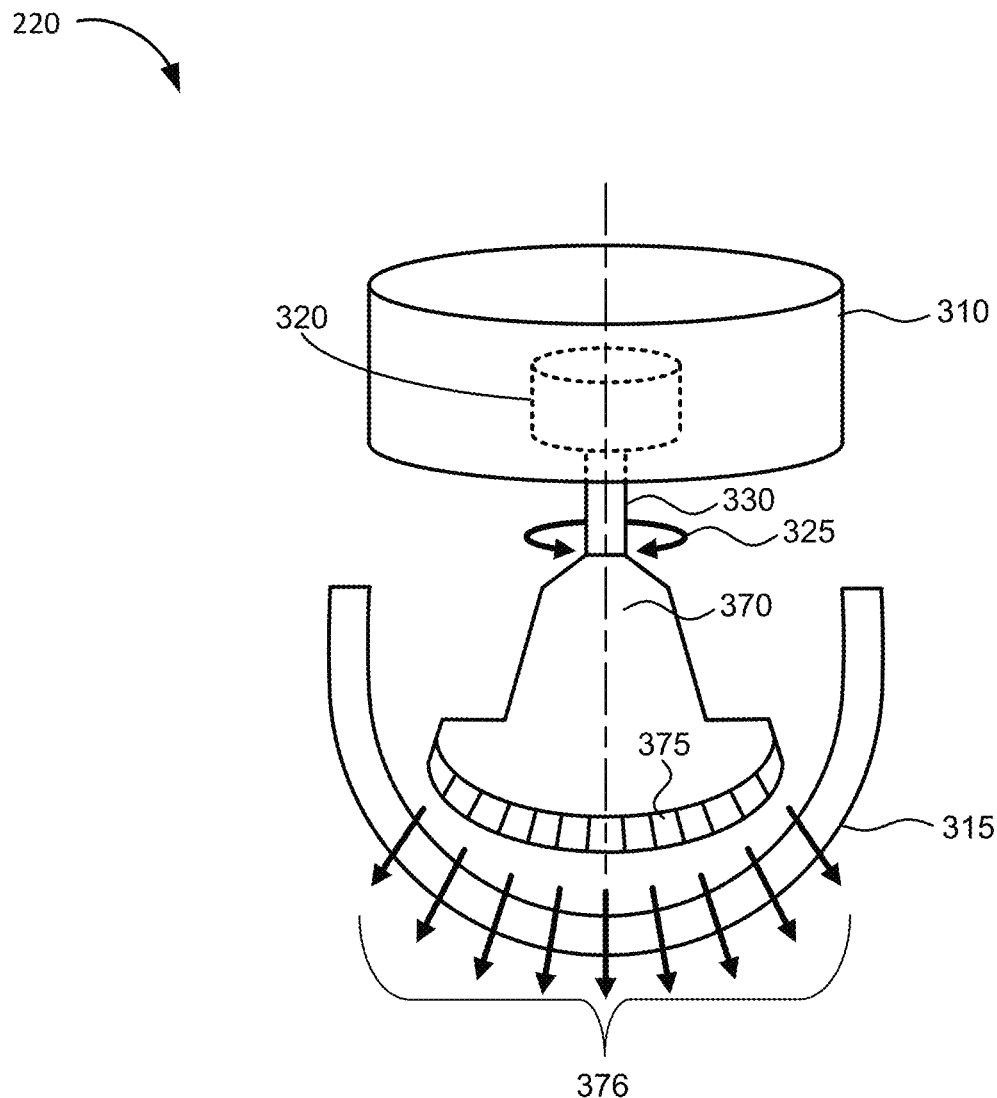

FIG. 3B is a diagram of a second exemplary implementation of ultrasound probe 220 according to an implementation described herein. As shown in FIG. 3B, ultrasound probe 220 may include a one-dimensional (1D) array of transducer elements coupled to a rotation motor. In this implementation, ultrasound probe 220 may include a base 310 connected to dome 315, a theta motor 320, a spindle 330, and a transducer bucket 370 with a 1D transducer array 375. Theta motor 320 and/or 1D transducer array 375 may include wired or wireless electrical connections that electrically connect theta motor 320 and/or 1D transducer array 375 to controller unit 210.

Base 310 may house theta motor 320 and provide structural support to ultrasound probe 220. Base 310 may connect to dome 315 and may form a seal with dome 315 to protect the components of ultrasound probe 220 from the external environment. Theta motor 320 may rotate spindle 330 with respect to base 310 in longitudinal direction with respect to 1D transducer array 375 by rotating around theta rotational plane 325. Spindle 330 may terminate in transducer bucket 370. 1D transducer array 375 may be mounted to transducer bucket 370. 1D transducer array 375 may include a curved 1D array of piezoelectric transducers, capacitive transducers, and/or other types of ultrasound transducers. 1D transducer array 375 may convert electrical signals to ultrasound signals at a particular ultrasound frequency or range of ultrasound frequencies, may receive reflected ultrasound signals (e.g., echoes, etc.), and may convert the received ultrasound signals to electrical signals. Each element of 1D transducer array 375 may transmit and receive ultrasound signals in a particular direction of a set of directions, illustrated as item 376 in FIG. 3B. Thus, together, the elements of 1D transducer array 375 may generate ultrasound image data for a particular plane. In a 3D scan mode, theta motor 320 may cycle through a set of planes one or more times to obtain a full 3D scan of an area of interest. In each particular plane of the set of planes, 1D transducer array 375 may obtain ultrasound image data for the particular plane. In some implementations, ultrasound probe 220 may not include theta motor 320 and/or dome 315. For example, ultrasound probe 220 may correspond to a hand-held probe that is moved manually by a user to different positions.

Figure 3C:
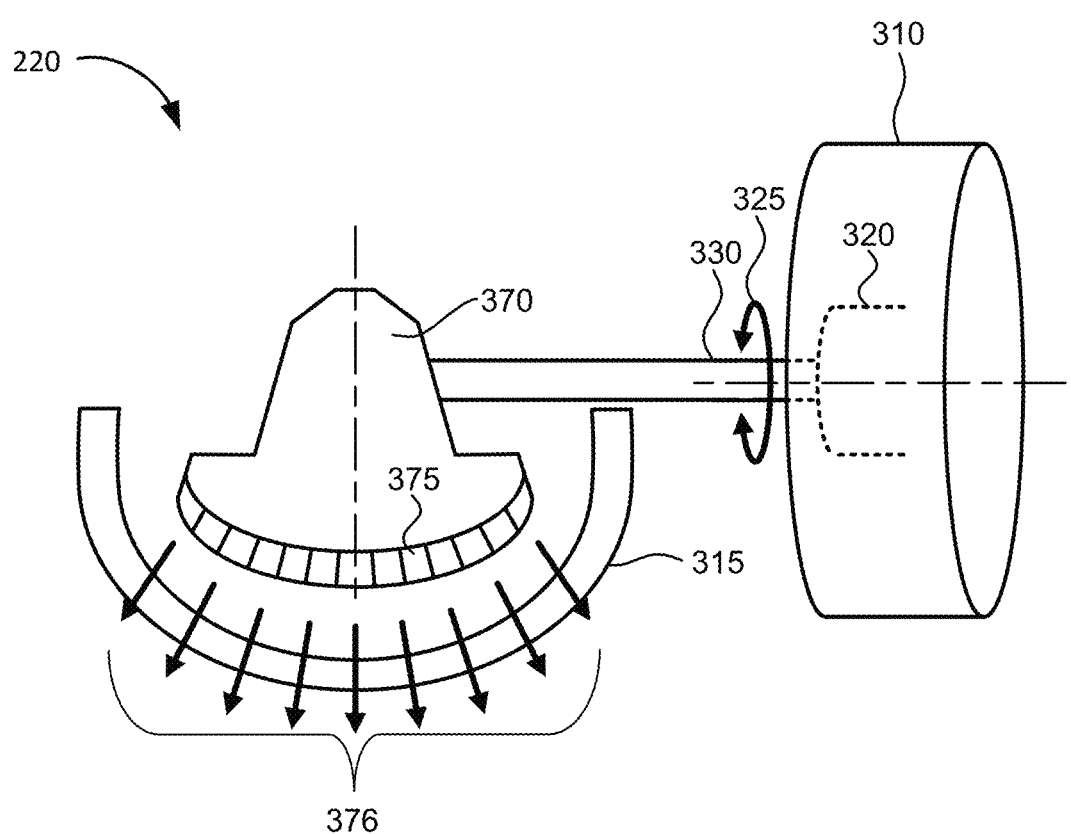

FIG. 3C is a diagram of a third exemplary ultrasound probe 220 according to an implementation described herein. While in second exemplary ultrasound probe 220 of FIG. 2B, 1D transducer array 375 rotates around spindle 330 in a longitudinal direction with respect to 1D transducer array 375, in third exemplary ultrasound probe 220 of FIG. 3C, 1D transducer array 375 rotates around spindle 330 in transverse direction with respect to 1D transducer array 375, causing 1D transducer array 375 to move back and forth in a fan-like motion. As shown in FIG. 3C, ultrasound probe 220 may include 1D transducer array 375 mounted to transducer bucket 370 with base 310, theta motor 320, and spindle 330 mounted in a horizontal direction with respect to 1D transducer array 375 and positioned perpendicularly to the center of set of directions 376. Thus, theta motor 320 may rotate spindle 330 with respect to base 310 in a transverse direction with respect to 1D transducer array 375 by rotating around theta rotational plane 325, causing 1D transducer array 375 to move back and forth in a fan-like motion.

Figure 3D:
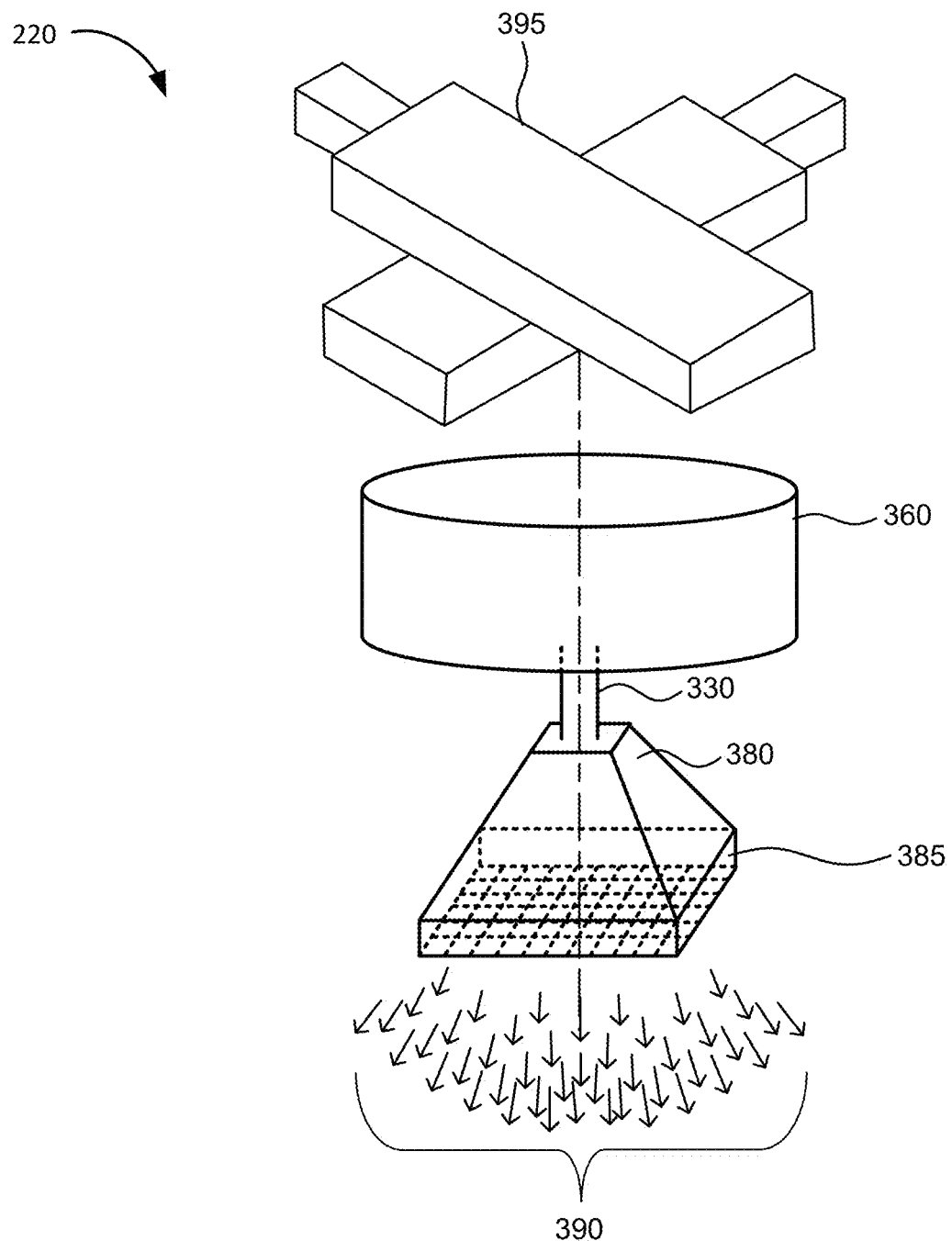

FIG. 3D is a diagram of a fourth exemplary ultrasound probe 220 according to an implementation described herein. As shown in FIG. 3D, ultrasound probe 220 may include a two-dimensional (2D) array of transducer elements. In this implementation, ultrasound probe 220 may include a base 310, a spindle 330, and a transducer bucket 380 with a 2D transducer array 385. 2D transducer array 385 may include wired or wireless electrical connections that electrically connects 2D transducer array 385 to controller unit 210.

Base 310 may provide structural support to ultrasound probe 220 and secure spindle 330. Spindle 330 may terminate in transducer bucket 380. 2D transducer array 385 may be mounted to transducer bucket 380. 2D transducer array 385 may include a 2D array of piezoelectric transducers, capacitive transducers, and/or other types of ultrasound transducers. 2D transducer array 385 may convert electrical signals to ultrasound signals at a particular ultrasound frequency or range of ultrasound frequencies, may receive reflected ultrasound signals (e.g., echoes, etc.), and may convert the received ultrasound signals to electrical signals. Each element of 2D transducer array 385 may transmit and receive ultrasound signals in a particular direction of a set of directions, illustrated as item 390 in FIG. 3D. Thus, together, the elements of 2D transducer array 385 may generate ultrasound image data for multiple planes to generate a 3D ultrasound scan. In other words, 2D transducer array 385 may be controlled to tilt an ultrasound beam electronically in a particular direction. In a 3D scan mode, 2D transducer array 385 may cycle through sets of 1D sets of transducer elements one or more times to obtain a full 3D scan of an area of interest. Alternatively, multiple sets of 1D sets of transducer elements, or even all of the transducer elements, of 2D transducer array 385 may be activated substantially simultaneously to obtain a full 3D scan of the area of interest.

In some implementations, ultrasound probe 220 may include a motor assembly 395. Motor assembly 395 may include a first motor configured to move ultrasound probe 220 in an X direction and a second motor configured to move ultrasound probe 220 in a Y direction. Thus, if ultrasound probe 220 includes motor assembly 395, rather than being held by an operator, ultrasound probe 220 may be controlled by controller unit 210 to automatically perform a full scan of a patient's breast area. In other implementations, motor assembly 395 may include a single linear motor. In yet other implementations, motor assembly 395 may include a rotating motor. In some implementations, motor assembly 220 may be attached to an articulating arm which may be used to place ultrasound probe 220 in position over a patient's breast area (and/or another body area). In other implementations, motor assembly 220 may be located in a recession of a table. A patient may lie prone on the table with the patient's breast area positioned over the recession, whereupon motor assembly 220 may be controlled to move ultrasound probe 220 within the recession to scan the patient's breast area. While not shown in FIG. 3A, 3B, or 3C, in other implementations, ultrasound probe 220 of FIG. 3A, 3B, or 3C may also include motor assembly 395 to automate a full scan of a patient's breast area (and/or another area of the patient's body).

Although FIGS. 3A, 3B, 3C, and 3D show exemplary components of ultrasound probe 220, in other implementations, ultrasound probe 220 may include fewer components, different components, additional components, or differently arranged components than depicted in FIGS. 3A, 3B, 3C, and 3D. Additionally or alternatively, one or more components of ultrasound probe 220 may perform one or more tasks described as being performed by one or more other components of ultrasound probe 220.

FIG. 4A is a diagram of a first exemplary depth camera 230 that uses a structured-light 3D scanner to obtain depth information for a captured image. As shown in FIG. 4A, depth camera 230 may include a digital camera 410, a structured light projector 420, a depth sensor 430, and a handle 440. Digital camera 410 may include an array of digital image sensors, such as charged-coupled device (CCD) sensors, complementary metal-oxide-semiconductor (CMOS) sensors, and/or other types of digital image sensors configured to capture color optical images. For example, digital camera 410 may obtain RGB values for each pixel in a captured optical image.

Structured light projector 420 may project patterns of IR beams on a scene being photographed and depth sensor 430 may include one or more IR sensors to sense reflected IR beams and measure the distance traveled by each IR beam to determine depth information for each pixel. The depth (D) information is correlated to the RGB values to generate RGB-D information for each pixel. Handle 440 may enable an operator to hold depth camera 230 and aim the depth camera at an area of interest for a patient, such as the patient's breast area. Depth camera 230 may include wired or wireless electrical connections that electrically connects depth camera 230 to controller unit 210.

FIG. 4B is a diagram of a second exemplary depth camera 230 that uses an array of individual cameras. As shown in FIG. 4B, depth camera 230 may include a camera array 450 and handle 440. Camera array 450 may include an array of individual cameras that each include an array of digital image sensors, such as CCD sensors, CMOS sensors, and/or other types of digital image sensors configured to capture color optical images. For example, camera array 450 may include a 4×4 array of 16 cameras. The array of cameras may be used to obtain depth information for an image through, for example, parallax detection and/or super-resolution techniques. Handle 440 may enable an operator to hold depth camera 230 and aim the depth camera at an area of interest for a patient, such as the patient's breast area. Depth camera 230 may include wired or wireless electrical connections that electrically connects depth camera 230 to controller unit 210.

Figure 4C:
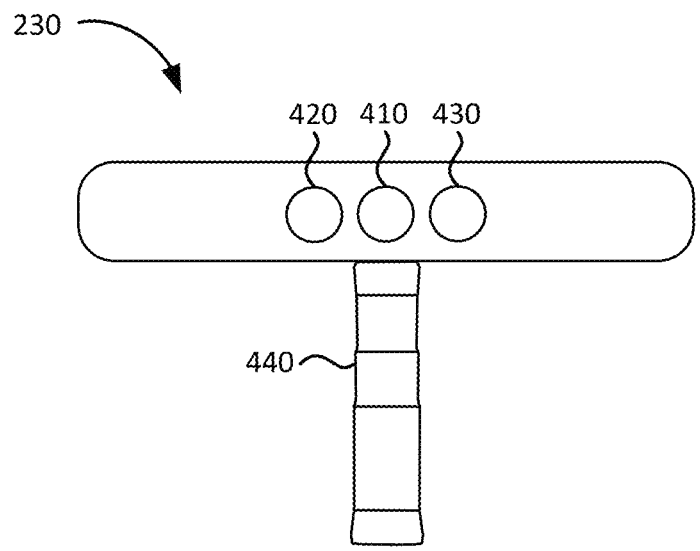
Figure 4C:
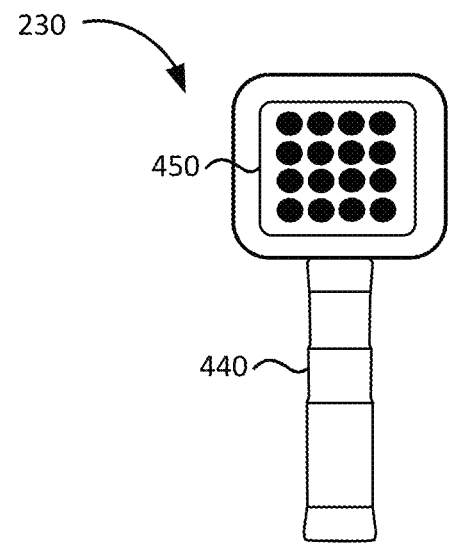
Figure 4C:
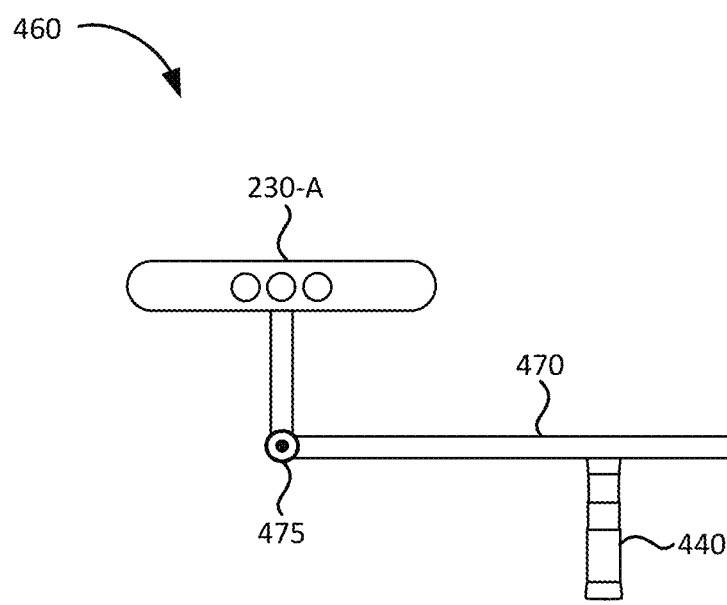

FIG. 4C is a diagram of a third exemplary depth camera system 460 that uses a first depth camera 230-A and a second depth camera 230-B mounted on a frame 470 with handle 440. Frame 470 may include adjustable connections 475 that may be used to move first depth camera 230-A and second depth camera 230-B to particular positions to scan a patient's breast area. In some implementations, adjustable connections 475 may include motors that may be electronically controlled by controller unit 210 to move first depth cameras 230-A and 230-B. Depth camera system 460 may facilitate capturing the whole breast area at a close range within a smaller time period than a single depth camera 230.

Although FIGS. 4A, 4B, and 4C show exemplary components of depth camera 230, in other implementations, depth camera 230 may include fewer components, different components, additional components, or differently arranged components than depicted in FIGS. 4A, 4B, and 4C. Additionally or alternatively, one or more components of depth camera 230 may perform one or more tasks described as being performed by one or more other components of depth camera 230. For example, in some implementations, depth camera 230 may include one or more gyroscopes to track the position of depth camera 230 during image capture.

Figure 5:
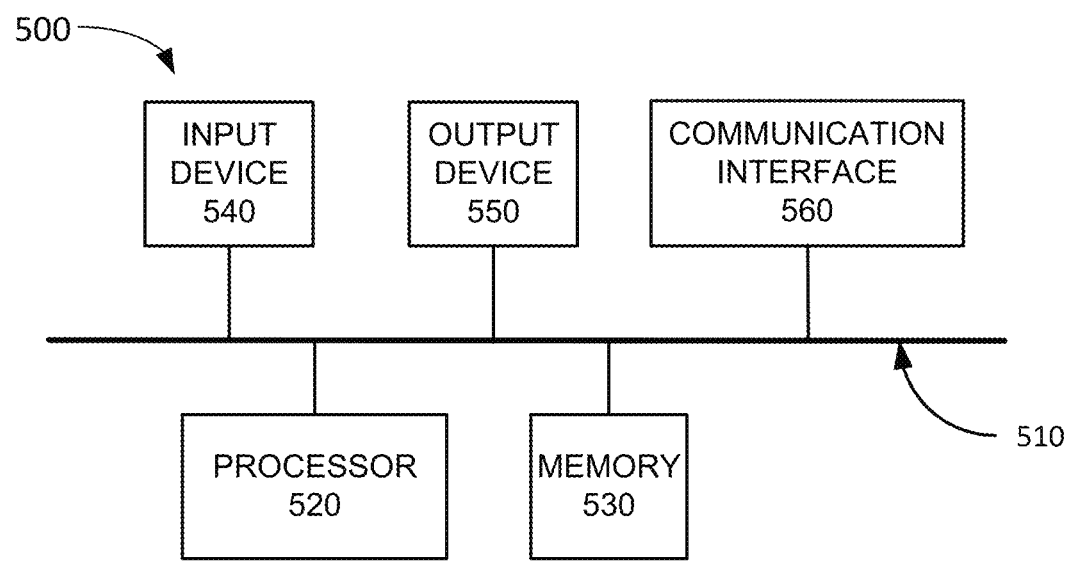
FIG. 5 is a diagram illustrating exemplary components of a device that included in one or more components of the system of FIGS. 2A and 2B.

FIG. 5 is a diagram illustrating example components of a device 500 according to an implementation described herein. Controller unit 210, ultrasound probe 220, and/or depth camera 230 may each include one or more devices 500. As shown in FIG. 5, device 500 may include a bus 510, a processor 520, a memory 530, an input device 540, an output device 550, and a communication interface 560.

Bus 510 may include a path that permits communication among the components of device 500. Processor 520 may include any type of single-core processor, multi-core processor, microprocessor, latch-based processor, and/or processing logic (or families of processors, microprocessors, and/or processing logics) that interprets and executes instructions. In other embodiments, processor 520 may include an application-specific integrated circuit (ASIC), a field-programmable gate array (FPGA), and/or another type of integrated circuit or processing logic.

Memory 530 may include any type of dynamic storage device that may store information and/or instructions, for execution by processor 520, and/or any type of non-volatile storage device that may store information for use by processor 520. For example, memory 530 may include a random access memory (RAM) or another type of dynamic storage device, a read-only memory (ROM) device or another type of static storage device, a content addressable memory (CAM), a magnetic and/or optical recording memory device and its corresponding drive (e.g., a hard disk drive, optical drive, etc.), and/or a removable form of memory, such as a flash memory.

Input device 540 may allow an operator to input information into device 500. Input device 540 may include, for example, a keyboard, a mouse, a pen, a microphone, a remote control, an audio capture device, an image and/or video capture device, a touch-screen display, and/or another type of input device. In some embodiments, device 500 may be managed remotely and may not include input device 540. In other words, device 500 may be "headless" and may not include a keyboard, for example.

Output device 550 may output information to an operator of device 500. Output device 550 may include a display, a printer, a speaker, and/or another type of output device. For example, device 500 may include a display, which may include a liquid-crystal display (LCD) for displaying content to the customer. In some embodiments, device 500 may be managed remotely and may not include output device 550. In other words, device 500 may be "headless" and may not include a display, for example.

Communication interface 560 may include a transceiver that enables device 500 to communicate with other devices and/or systems via wireless communications (e.g., radio frequency, infrared, and/or visual optics, etc.), wired communications (e.g., conductive wire, twisted pair cable, coaxial cable, transmission line, fiber optic cable, and/or waveguide, etc.), or a combination of wireless and wired communications. Communication interface 560 may include a transmitter that converts baseband signals to radio frequency (RF) signals and/or a receiver that converts RF signals to baseband signals. Communication interface 560 may be coupled to an antenna for transmitting and receiving RF signals.

Communication interface 560 may include a logical component that includes input and/or output ports, input and/or output systems, and/or other input and output components that facilitate the transmission of data to other devices. For example, communication interface 560 may include a network interface card (e.g., Ethernet card) for wired communications and/or a wireless network interface (e.g., a WiFi)

card for wireless communications. Communication interface 560 may also include a universal serial bus (USB) port for communications over a cable, a Bluetooth™ wireless interface, a radio-frequency identification (RFID) interface, a near-field communications (NFC) wireless interface, and/or any other type of interface that converts data from one form to another form.

As will be described in detail below, device 500 may perform certain operations relating to implant assessment using ultrasound and/or optical images. Device 500 may perform these operations in response to processor 520 executing software instructions contained in a computer-readable medium, such as memory 530. A computer-readable medium may be defined as a non-transitory memory device. A memory device may be implemented within a single physical memory device or spread across multiple physical memory devices. The software instructions may be read into memory 530 from another computer-readable medium or from another device. The software instructions contained in memory 530 may cause processor 520 to perform processes described herein. Alternatively, hard-wired circuitry may be used in place of, or in combination with, software instructions to implement processes described herein. Thus, implementations described herein are not limited to any specific combination of hardware circuitry and software.

Although FIG. 5 shows exemplary components of device 500, in other implementations, device 500 may include fewer components, different components, additional components, or differently arranged components than depicted in FIG. 5. Additionally or alternatively, one or more components of device 500 may perform one or more tasks described as being performed by one or more other components of device 500.

Figure 6:
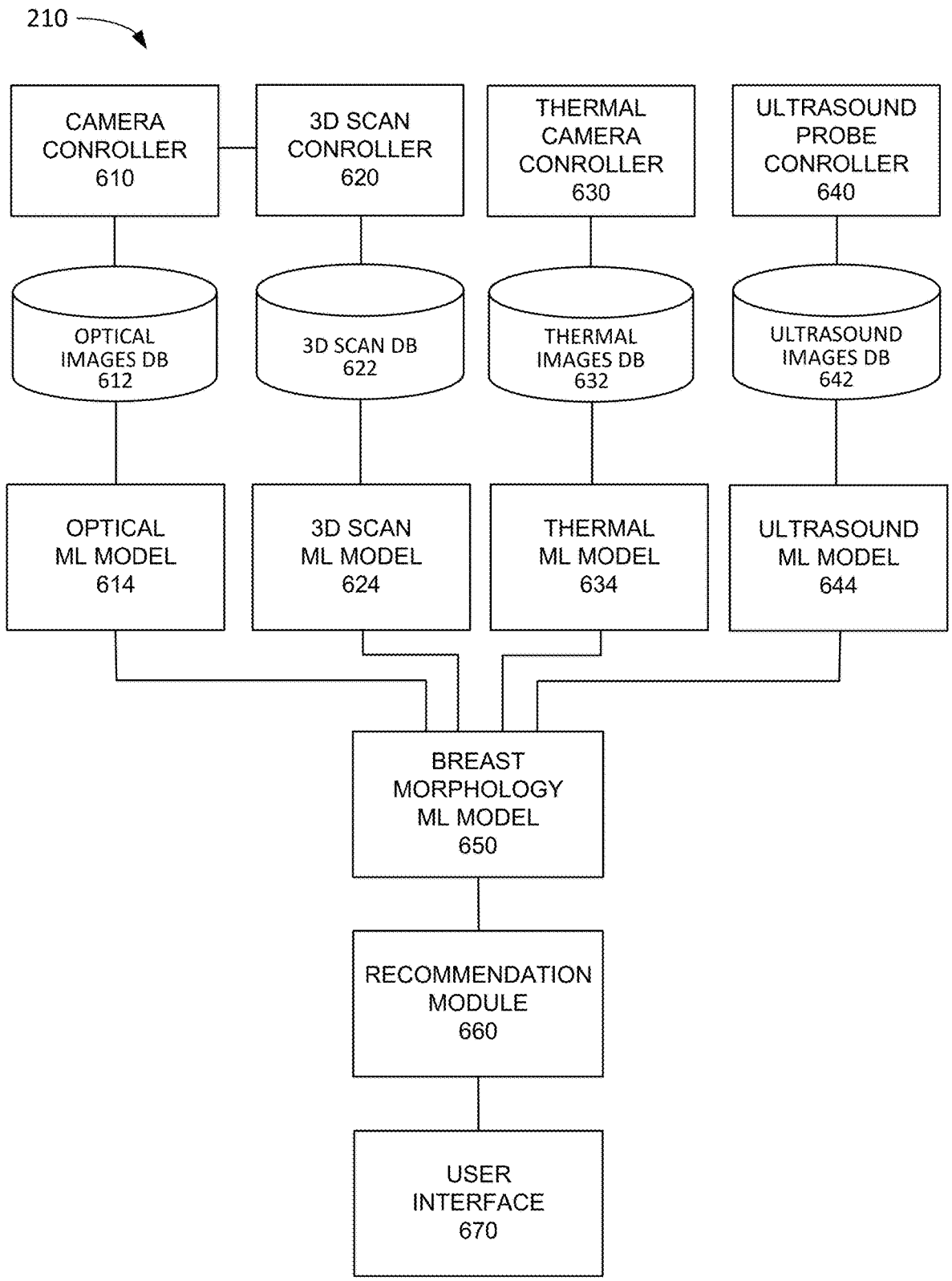
FIG. 6 is a diagram illustrating exemplary functional components of the system of FIGS. 1A and 1B.

FIG. 6 is a diagram illustrating exemplary functional components of controller unit 210. The functional components of controller unit 210 may be implemented, for example, via processor 520 executing instructions from memory 530. Alternatively, some or all of the functional components of controller unit 210 may be implemented via hard-wired circuitry. As shown in FIG. 6, controller unit 210 may include a camera controller 610, an optical images DB 612, an optical machine learning (ML) model 614, a 3D scan controller 620, a 3D scan DB 622, a 3D scan ML model 624, a thermal camera controller 630, a thermal images DB 632, a thermal ML model 634, an ultrasound probe controller 640, a ultrasound images DB 642, a ultrasound ML model 644, a breast morphology ML model 650, a recommendation module 660, and a user interface 670.

Camera controller 610 may be configured to control depth camera 230 and to collect optical image data from depth camera 230. For example, camera controller 620 may instruct a user to position depth camera 230 in particular locations to take a series of optical images and store the optical images in optical images DB 612.

3D scan controller 620 may control depth camera 230 to obtain 3D scan images. For example, 3D scan controller 620 may keep track of the position of depth camera 230 to guide the user to capture images from several angles. Depth camera 230 may store the position information associated with each captured optical image. The position information may be used to generate a point cloud and/or 3D triangular mesh of the patient's breast area. 3D scan controller 620 may store captured 3D scan images in 3D scan images DB 622. In some implementations, optical and 3D scan information may be stored together as RGB-D images.

Thermal camera controller 630 may control thermal camera 240 to obtain thermal camera images. For example, thermal camera controller 630 may keep track of the position of thermal camera 240 to guide the user to capture thermal images from several angles. Thermal camera controller 630 may store captured thermal camera images in thermal images DB 632.

Ultrasound probe controller 640 may be configured to control ultrasound probe 220 and to collect ultrasound image data from ultrasound probe 220. For example, ultrasound probe controller 640 may perform a 3D scan of a sector in a sector grid associated with a patient's breast area by generating ultrasound images in particular planes by controlling one or more motors and/or particular transducers of ultrasound probe 220. For a particular sector, ultrasound probe controller 640 may control ultrasound probe 220 to perform a 3D scan that includes all radial, antiradial, sagittal, and transverse planes in the sector. Furthermore, ultrasound probe controller 640 may be configured to control ultrasound probe 220 to obtain elastography ultrasound images. Ultrasound probe controller 640 may store obtained ultrasound images in ultrasound images DB 642.

Optical ML model 614 may include a trained CNN model and/or another type of ML model. Optical ML model 614 may be trained to process and characterize optical images from optical images DB 612. For example, optical ML model 614 may pre-process optical images before performing classification and/or feature extraction. Optical ML model 614 may be configured to classify one or more optical images into a particular quantitative clinical grading value.

3D scan ML model 624 may include a trained CNN model and/or another type of ML model. 3D scan ML model 624 may be trained to process and characterize 3D scan images from 3D scan images DB 622. For example, 3D scan ML model 624 may pre-process 3D scan images before performing classification and/or feature extraction, such as generating a point cloud and/or a 3D triangular mesh based on one or more 3D scan images. 3D scan ML model 624 may be configured to classify one or more 3D scan images into a particular quantitative clinical grading value. Additionally, or alternatively, 3D scan ML model 624 may be configured to generate a 3D geometric feature plot; perform segmentation of an implant capsule, a rupture area and/or a fluid collection; and/or generate a 3D shape of the implant capsule, rupture area, and/or fluid collection based on the segmentation.

Thermal ML model 634 may include a trained CNN model and/or another type of ML model. Thermal ML model 634 may be trained to process and characterize thermal camera images from thermal images DB 632. For example, thermal ML model 634 may pre-process thermal camera images before performing classification and/or feature extraction. Thermal ML model 634 may be configured to classify one or more thermal camera images into a particular quantitative clinical grading value. Additionally, or alternatively, thermal ML model 634 may be configured to generate a temperature variation plot; generate a 3D geometric feature plot; perform segmentation of an implant capsule, a rupture area and/or a fluid collection; and/or generate a 3D shape of the implant capsule, rupture area, and/or fluid collection based on the segmentation.

Ultrasound ML model 644 may include a trained CNN model and/or another type of ML model. Ultrasound ML model 644 may be trained to process and characterize ultrasound images from ultrasound images DB 642. For example, ultrasound ML model 644 may pre-process ultrasound images before performing classification and/or feature extraction. Ultrasound ML model 644 may be configured to classify one or more ultrasound images into a particular quantitative clinical grading value. Additionally, or alternatively, ultrasound ML model 644 may be configured to generate a 3D geometric feature plot; perform segmentation of an implant capsule, a rupture area and/or a fluid collection; generate a stiffness plot based on elastography images; and/or generate a 3D shape of the implant capsule, rupture area, and/or fluid collection based on the segmentation.

Furthermore, ultrasound ML model 644 may include a CNN model and/or another type of ML model trained to perform segmentation to identify the boundary of an implant capsule in an ultrasound image, to determine a thickness of the implant capsule, and/or to determine a radial fold count for the implant capsule. Additionally, or alternatively, ultrasound ML model 644 may include a CNN model and/or another type of ML model trained to identify an extracapsular rupture, a diffuse snowstorm sign associated with an extracapsular rupture, an intracapsular rupture, a capsular contracture, a fluid collection (e.g., a seroma, a hematoma, a breast abscess, etc.), a breast mass, and/or other types of pathologies that may be associated with a breast or a breast implant in an ultrasound image.

Breast morphology ML model 650 may include a trained CNN model and/or another type of ML model. Breast morphology ML model 650 may take as input the output of one or more of optical ML model 614, 3D scan ML model 624, thermal ML model 634, and/or ultrasound ML model 644. Alternatively, in some implementations, one or more of optical ML model 614, 3D scan ML model 624, thermal ML model 634, and/or ultrasound ML model 644 and breast morphology ML model 650 may be combined into a single ML model.

Breast morphology ML model 650 may be trained to identify a change in the morphology or integrity of a patient's breast and/or breast implant. For example, breast morphology model 670 may generate a quantitative clinical grading value based on a set of images, such as a Baker class value, an implant capsule thickness value, a radial fold count value, an implant capsule smoothness value, and/or another type of quantitative clinical grading value.

Additionally, or alternatively, breast morphology ML model 650 may be trained to generate a 3D geometrical feature plot. The 3D geometrical feature may include, for example, curvature, symmetry, smoothness, distance from a particular location, and/or another type of 3D geometrical feature. Furthermore, breast morphology ML model 650 may be trained to use the generated 3D geometrical feature plot to identify a lack of symmetry between a left and a right breast, to determine the size and/or volume of a breast, to determine the angle of a breast with respect to the patient's rib cage, to determine the distance between a point on a breast and a reference point on the patient's rib cage, to identify a volume region that has experienced contracture, to identify a volume region that has experienced a rupture, to identify volume a region of fluid collection, and/or to identify another feature within an optical image that includes depth information.

Furthermore, breast morphology ML model 650 may be trained to compare baseline optical, 3D scan, thermal camera, and/or ultrasound images for a patient's breast area, a baseline 3D geometrical feature plot, and/or a baseline 3D shape of an implant capsule with follow-up optical, 3D scan, thermal camera, and/or ultrasound images for the patient's breast area, a follow-up 3D geometrical feature plot, and/or a follow-up 3D shape of the implant capsule and output a quantitative clinical grading value based on the comparison. In some implementations, breast morphology ML model 650 may further output an image that has been segmented to identify the boundaries around areas in the patient's breast area that have changed from the baseline optical image to the follow-up optical image.

Recommendation module 660 may provide the output of breast morphology ML model 650 and may generate a recommendation for a particular type of medical intervention based on the output of breast morphology ML model 650. As an example, if breast morphology ML model 650 outputs a Baker class of 1 or 2, recommendation module 660 may recommend a non-surgical intervention to correct a capsular contracture, such as manual therapy, a steroid injection, or a drug prescription. As another example, if breast morphology ML model 650 outputs a Baker class of 3 or 4, recommendation module 660 may recommend surgical intervention to correct a capsular contracture. As yet another example, if breast morphology ML model 650 outputs an identified seroma, recommendation module 660 may recommend an aspiration procedure. As yet another example, if breast morphology ML model 650 outputs a particular thickness value of an implant capsule and/or a particular radial fold count value, recommendation module 660 may recommend a particular medical intervention based on the generated value.

User interface 670 may generate or include a user interface (e.g., a graphical user interface) that displays ultrasound images and/or optical images to a user via display 215, displays recommendations to the user, and that is configured to receive selections and/or commands from the user via a touchscreen associated with display 215, via one or more control keys located on controller unit 210, on ultrasound probe 220, and/or depth camera 230, via a microphone included in controller unit 210, and/or via another type of input method.

For example, a user may select a particular type of ultrasound image to obtain, to perform a 3D ultrasound scan using a sector grid, select to perform an elastography ultrasound scan, select to capture optical and/or 3D scan images using depth camera 230, select to retrieve a patient record that includes previously obtained ultrasound and optical images, select to perform a machine learning model comparison of baseline and follow-up ultrasound, optical, 3D scan, and/or thermal, select to use a machine learning model to perform segmentation and analysis of an implant capsule, select to identify implant or breast pathologies using a machine learning model, and/or select to perform another type of function for which controller unit 210 has been configured.

Although FIG. 6 shows exemplary components of controller unit 210, in other implementations, controller unit 210 may include fewer components, different components, additional components, or differently arranged components than depicted in FIG. 6. Additionally, or alternatively, one or more components of controller unit 210 may perform one or more tasks described as being performed by one or more other components of controller unit 210.

Figure 7:
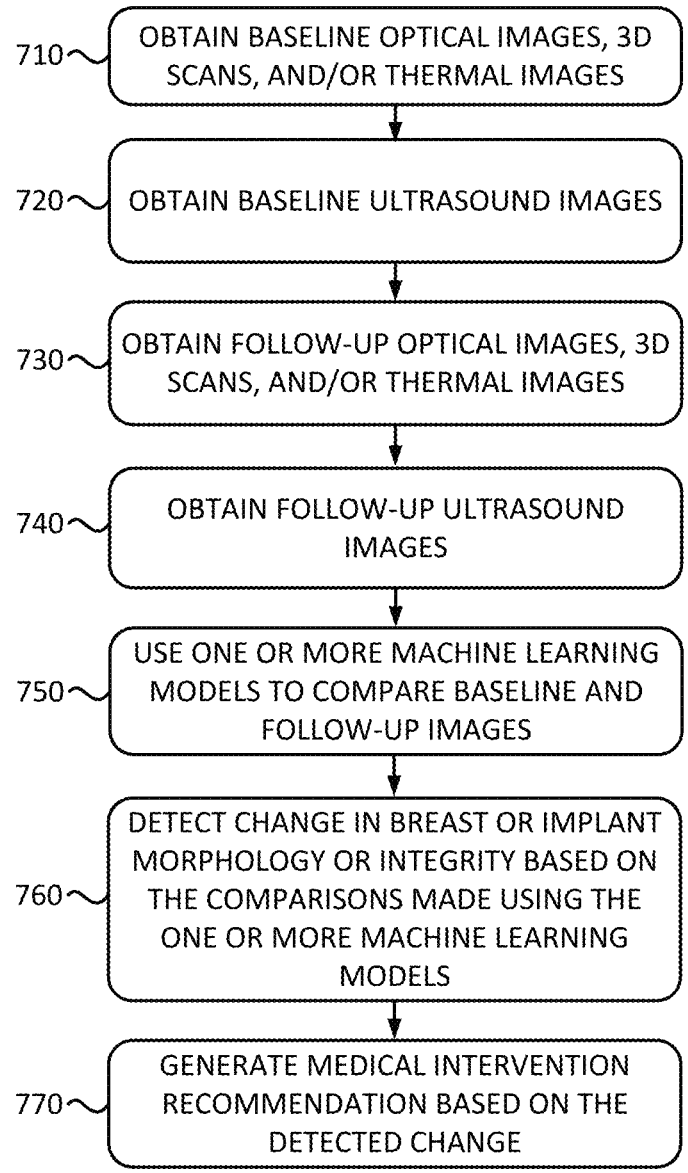
FIG. 7 is a flowchart of a process for implant assessment using machine learning according to an implementation described herein.

FIG. 7 is a flowchart of a process for implant assessment using machine learning according to an implementation described herein. In some implementations, the process of FIG. 7 may be performed by ultrasound system 201 or 202. In other implementations, some or all of the process of FIG. 7 may be performed by another device or a group of devices separate from ultrasound system 201 or 202.

The process of FIG. 7 may include obtaining baseline optical, 3D scan, and/or thermal camera images (block 710).

For example, controller unit 210 may guide a user, via display 115 and/or a speaker, to capture a set of optical and/or 3D scan images via depth camera 230. In some implementations, the user may be instructed to continuously move depth camera 230 around the patient's breast area while depth camera 230 captures a set of optical images. In other implementations, the user may be instructed to position depth camera 230 at particular angles with respect to the patient's breast area. In yet other implementations, the patient may be asked to move to different positions while depth camera 230 remains stationary. Furthermore, the patient may be instructed to assume different positions, such as a supine position, an inclined position, an upright position, etc. A similar procedure may be performed using thermal camera 240 to capture thermal camera images.

In some implementations, depth camera 230 may include a laser guide to facilitate aiming depth camera 230 at the correct location on the patient's body. Furthermore, in some implementations, the user may be guided to obtain a first set of 3D scan images from a first distance away from the patient and to obtain a second set of 3D scan images from a second distance away from the patient. The obtained 3D scan images may be stored in 3D scan images DB 622 in connection with information identifying the patient, information identifying the date when the images were taken, information identifying the images as baseline images, and/or other types of information associated with the optical images.

Baseline ultrasound images may be obtained (block 720). For example, controller unit 210 may guide a user, via display 115 and/or a speaker, to capture a set of ultrasound images via ultrasound probe 110. Controller unit 210 may generate a sector grid and may guide the user to perform a 3D ultrasound scan for each sector in the sector grid. Display 115 may display a progress of the scan by indicating which sectors have already been scanned. Additionally, the user may select, or be instructed to, obtain a set of elastography ultrasound images using ultrasound probe 220. In other implementations, ultrasound probe 220 may include a gyroscope and/or another type of position tracking device and the user may be guided to move ultrasound probe 220 as a brush by filling in a bull's eye plot centered on the patient's breast. The obtained ultrasound imaged may be stored in ultrasound images DB 642 in connection with information identifying the patient, information identifying the date when the images were taken, information identifying the images as baseline images, and/or other types of information associated with the ultrasound images.

Follow-up optical, 3D scan, and/or thermal camera images may be obtained (block 730) and follow-up ultrasound images may be obtained (block 740). For example, the patient may return at a later time for a follow-up visit. Follow-up optical, 3D scan, and/or thermal camera images and ultrasound images of the patient's breast area may be obtained during the follow-up visit and stored in optical images DB 612, 3D scan images DB 622, thermal images DB 632, and/or ultrasound image DB 642 similarly to as described above with respect to blocks 710 and 720.

One or more machine learning models may be used to compare the baseline and follow-up images (block 750) and a change in breast or implant morphology or integrity may be detected based on the comparisons made using the one or more machine learning models (block 760). For example, breast morphology ML model 650 may compare baseline ultrasound, optical, 3D scan, and/or thermal camera images of the patient's breast area, a baseline 3D geometrical feature plot, and/or a baseline 3D shape of an implant capsule, with follow-up ultrasound, optical, 3D scan, and/or thermal camera images of the patient's breast area, a follow-up 3D geometrical feature plot, and/or a follow-up 3D shape of an implant capsule.

In some implementations, breast morphology ML model 650 may output a quantitative clinical grading value based on the comparison. In other implementations, breast morphology ML model 650 may classify the input into another type of class from a set of classes, such as whether a rupture is present, a type of rupture, whether a particular breast or implant pathology is present, and/or another type of classification.

A medical intervention recommendation may be generated based on the detected change (block 770). For example, recommendation module 660 may provide the output of breast morphology ML model 650 and may generate a recommendation for a particular type of medical intervention based on the output of breast morphology ML model 650, such a recommendation based on a quantitative clinical grading value, a recommendation based on an identified pathology, and/or another type of recommendation.

In some implementations, implant assessment may be performed without obtaining baseline images. For example, breast morphology ML model 650 may obtain an ultrasound image of a patient's breast area, obtain at least one of an optical image of the patient's breast area, a three-dimensional (3D) scan image of the patient's breast area, or a thermal camera image of the patient's breast area, and compare the ultrasound image with the at least one of the optical image of the patient's breast area, the 3D scan image of the patient's breast area, or the thermal camera image of the patient's breast area.

Figure 8:
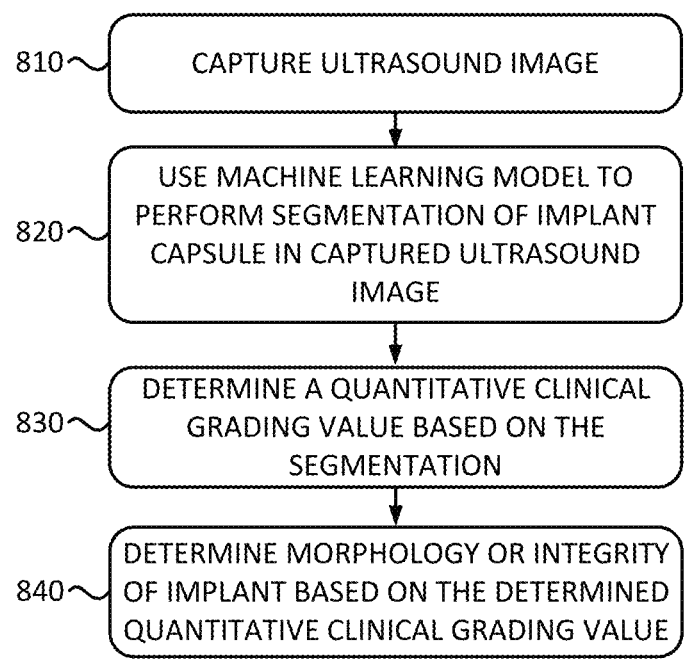
FIG. 8 is a flowchart of a process for characterizing an implant capsule using machine learning according to an implementation described herein.

FIG. 8 is a flowchart of a process for characterizing an implant capsule using machine learning according to an implementation described herein. In some implementations, the process of FIG. 8 may be performed by ultrasound system 201 or 202. In other implementations, some or all of the process of FIG. 8 may be performed by another device or a group of devices separate from ultrasound system 201 or 202.

The process of FIG. 8 may include capturing an ultrasound image (block 810). For example, ultrasound probe 220 may capture an ultrasound image of a patient's breast area. The ultrasound image may include an image of an implant capsule. A machine learning model may be used to perform a segmentation of an implant capsule in the captured ultrasound image (block 820). For example, ultrasound ML model 642 may perform segmentation on the captured ultrasound image to identify the boundaries of the implant capsule.

A quantitative clinical grading value may be determined based on the segmentation (block 830). For example, ultrasound ML model 642 may use the identified boundaries of the implant capsule to determine a set of thickness values for the implant capsule and to determine an average thickness for the implant capsule based on the determined set of thickness values. As another example, ultrasound ML model 642 may use the identified boundaries of the implant capsule to identify a set of radial folds. For example, ultrasound ML model 642 may identify points at which the curvature of a boundary of the implant capsule changes from positive to negative or vice versa. ultrasound ML model 642 may determine the number of radial folds per unit distance of the implant capsule. As yet another example, ultrasound ML model 642 may determine a smoothness value based on the segmented implant capsule.

A morphology or integrity of the implant may be determined based on the determined quantitative clinical grading value (block 850). For example, ultrasound ML model 642 may use the determined average thickness and radial fold count to classify the implant capsule into a particular Baker class and/or to determine whether the implant capsule is associated with capsular contracture.

Figure 9:
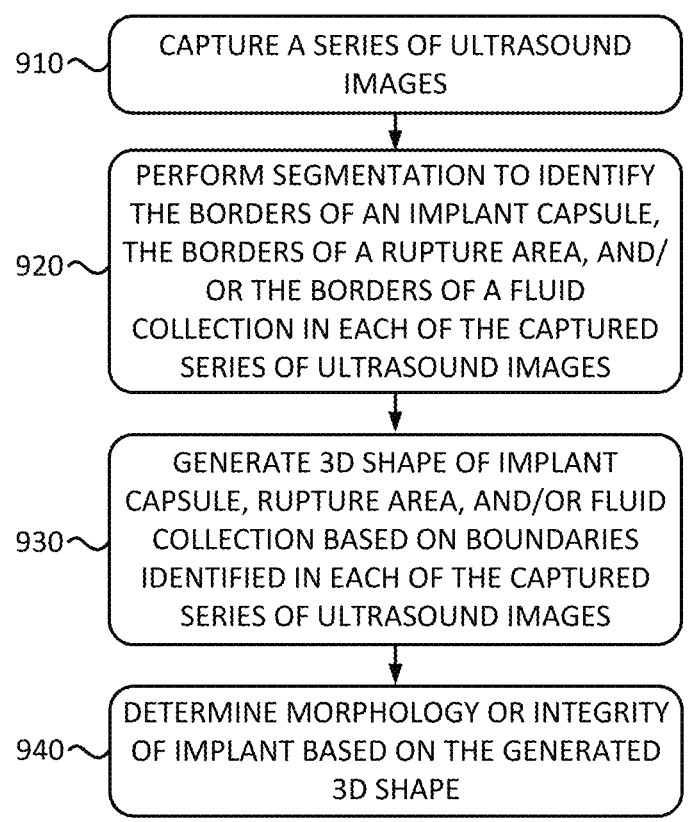
FIG. 9 is a flowchart of a process for characterizing the morphology or integrity of an implant using machine learning according to an implementation described herein.

FIG. 9 is a flowchart of a process for characterizing the morphology or integrity of an implant using machine learning according to an implementation described herein. In some implementations, the process of FIG. 9 may be performed by ultrasound system 201 or 202. In other implementations, some or all of the process of FIG. 9 may be performed by another device or a group of devices separate from ultrasound system 201 or 202.

The process of FIG. 9 may include capturing an ultrasound image (block 910). For example, ultrasound probe 220 may capture an ultrasound image, or a series of ultrasound images, of a patient's breast area. The ultrasound image may include an image of a breast implant. Segmentation may be performed to identify the borders of an implant capsule, a rupture area, and/or a fluid collection in each of a series of ultrasound images (block 920). For example, ultrasound ML model 644 may perform segmentation to identify the borders of an implant capsule, a rupture area, or a fluid collection.

A 3D shape of an implant capsule, rupture area, and/or a fluid collection may be generated based on the boundaries identified in each of the captured ultrasound images (block 930). For example, ultrasound ML model 644 may stitch together or connect the boundaries of a 3D shape of an implant capsule, rupture area, and/or a fluid collection using the boundaries identified in each of the ultrasound images and the position information associated with each ultrasound image.

A morphology or integrity of an implant may be determined based on the generated 3D shape (block 940). For example, breast morphology ML model 650 may determine a quantitative clinical grading based on the generated 3D shape and/or based on comparing the generated 3D shape to a previously generated baseline 3D shape.

Figure 10A:
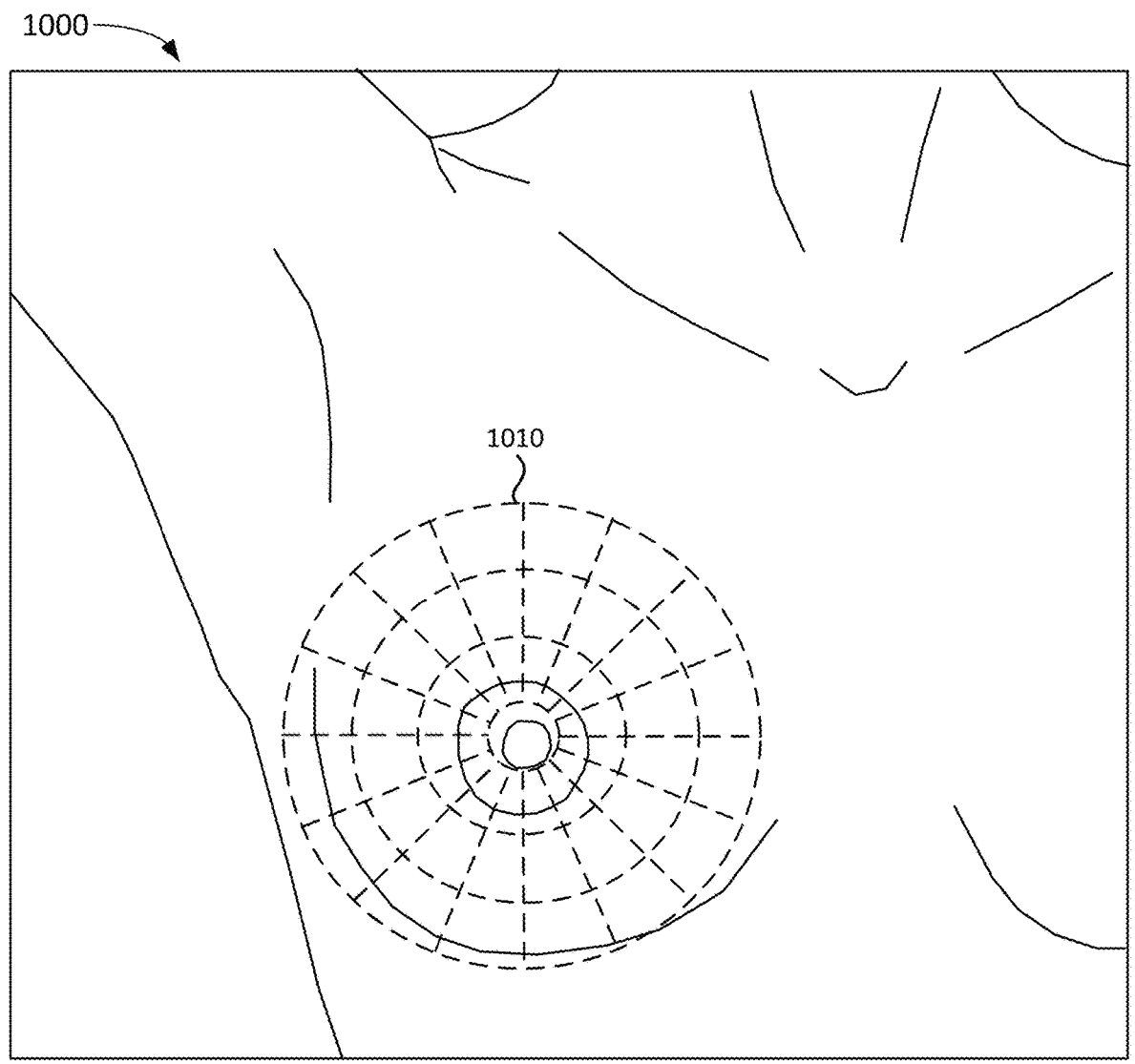
FIGS. 10A, 10B, 10C, and 10D are diagrams illustrating the use of a sector grid for performing an ultrasound scan according to an implementation described herein.

FIG. 10A is a diagram 1000 illustrating the use of a sector grid for performing an ultrasound. As shown in FIG. 10A, a sector grid 1010 may be overlaid over a patient's breast area. In some implementations, sector grid 1010 may include a physical marker, such as a sector grid printed onto a translucent thin film that is overlaid over the patient's breast area or a removable stencil that may be transferred onto the patient's skin. In other implementations, sector grid 1010 may be projected onto the patient's skin using a laser projector that is associated with controller unit 210. In yet other implementations, sector grid 1010 may be generated using augmented reality. For example, depth camera 230 (or another camera device) may be aimed at the patient's breast area and an image of the patient's breast area may be displayed by display 215 with sector grid 1010 overlaid over the image of the patient's breast area.

Sector grid 1010 may be used to keep track of which sectors of the patient's breast area have been scanned. Controller unit 210 may track the position of ultrasound probe 220 to determine which sector is being scanned and/or which sectors have already been scanned. For example, by aiming ultrasound probe 220 at a particular sector, a user may click trigger 224, activate a selection item on display 215, speak a command, or perform another type of action to perform a 3D scan of the particular sector. A 3D scan may capture all radial, anti-radial, sagittal, and/or transverse planes using a B-mode ultrasound image (and/or another type of ultrasound image).

Figure 10B:
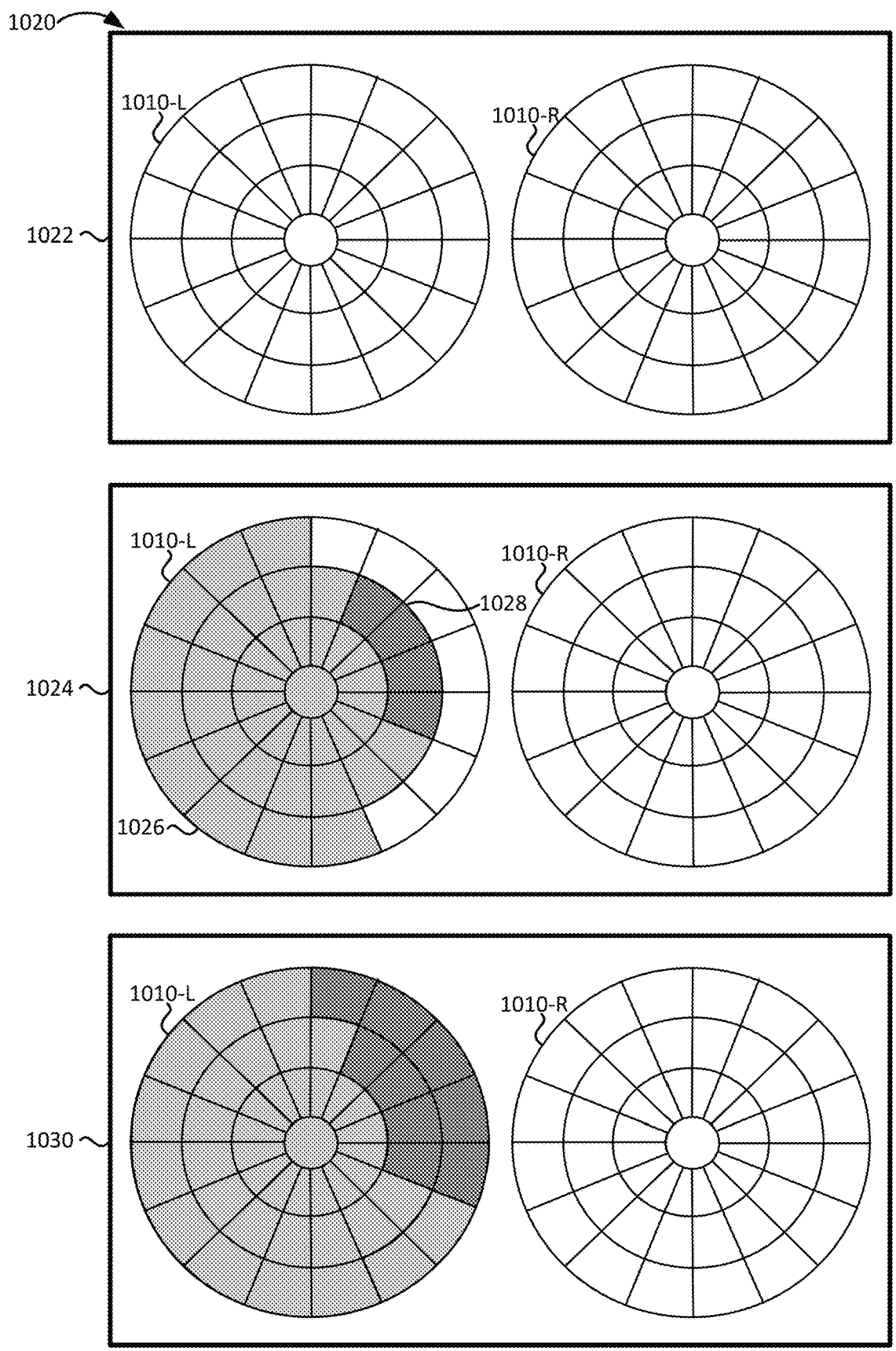

FIG. 10B is a diagram 1020 illustrating the progression of an ultrasound scan using sector grid 1010. As shown in FIG. 10B, a sector grid 1010-L may be associated with a left breast and a sector grid 1010-R may be associated with a right breast. A user interface 1022 on display 215 may initially depict empty sector grids 1010-L and 1010-R, indicating that no sectors have been scanned yet. As the user progresses with scanning the patient's breast area, user interface 1024 may display the progress of the scan. For example, a sector 1026 that has been scanned may be filled in with a particular shading, color, or pattern. Furthermore, a sector 1028 may be designated as a sector of interest with another shading, color, or pattern to indicate that one or more machine learning models have identified an object of interest in the sector, such as a change in the morphology or integrity of an implant, and/or an implant or breast pathology. When the user has scanned all the sectors, sector grid 1010 may be completely filled in with the particular shading, color, or pattern, as shown in user interface 1030. In some implementations, scanning of sector grid 1010 may be automated by controller unit 210 via motor assembly 395.

Figure 10C:
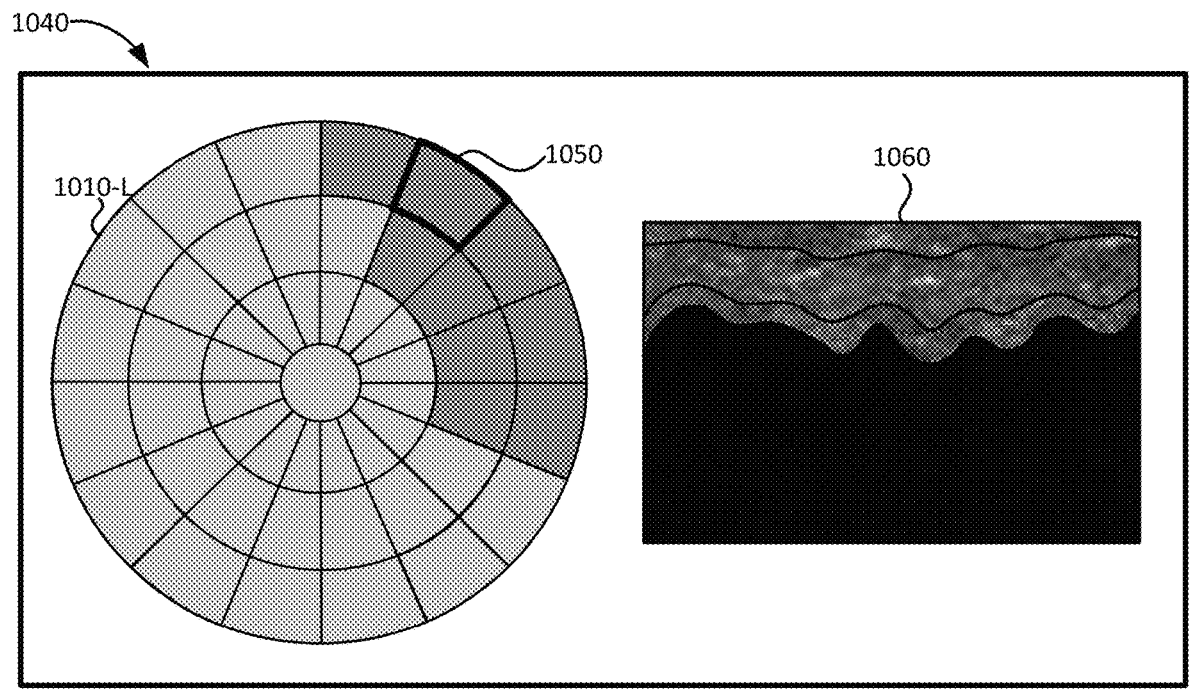

FIG. 10C is a diagram 1040 illustrating selection of a scanned sector to view an ultrasound image associated with the selected sector. In response to a user selecting a sector 1050, the sector may be highlighted and an ultrasound image 1060 associated with the sector may be displayed in the user interface. In some implementations, the user may scroll or flip through ultrasound images associated with the selected sector. While FIGS. 10A-10C illustrate a sector grid, in other implementations, other types of markers may be used to keep track of which areas of a patient's breast area have been scanned. For example, sector grid 1010 may include a dot pattern and/or another type of marker.

Figure 10D:
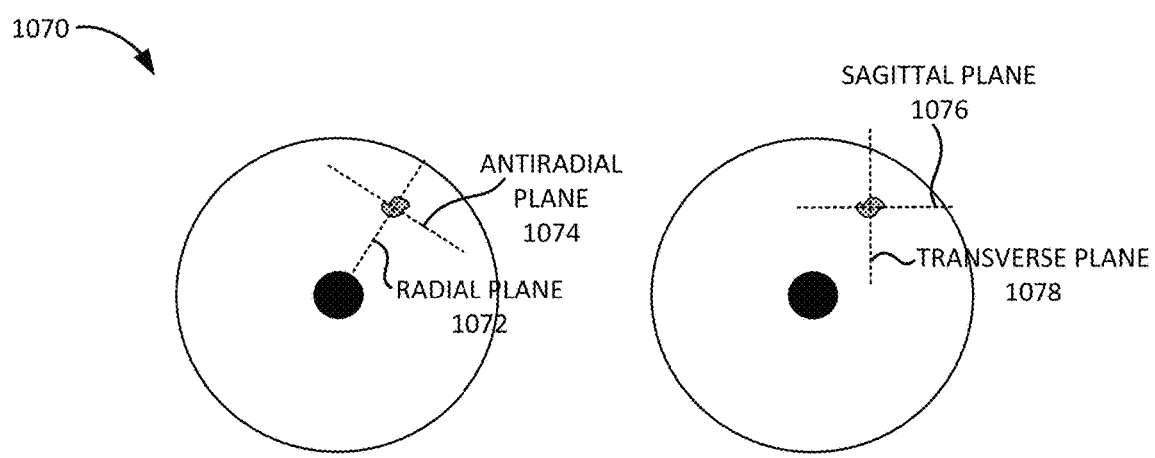

FIG. 10D is a diagram 1070 illustrating the planes of a 3D scan performed for each sector of sector grid 1010. Ultrasound probe 220 may perform a series of scans to generate a set of ultrasound images in a radial plane 1072 with respect to the breast. Ultrasound probe 220 may further perform a series of scans to generate a set of ultrasound images in an antiradial plane 1074 with respect to the breast. Moreover, ultrasound probe 220 may perform a series of scans to generate a set of ultrasound images in a sagittal plane 1076 with respect to the breast and a series of scans to generate a set of ultrasound images in a transverse plane 1078 with respect to the breast.

Figure 11:
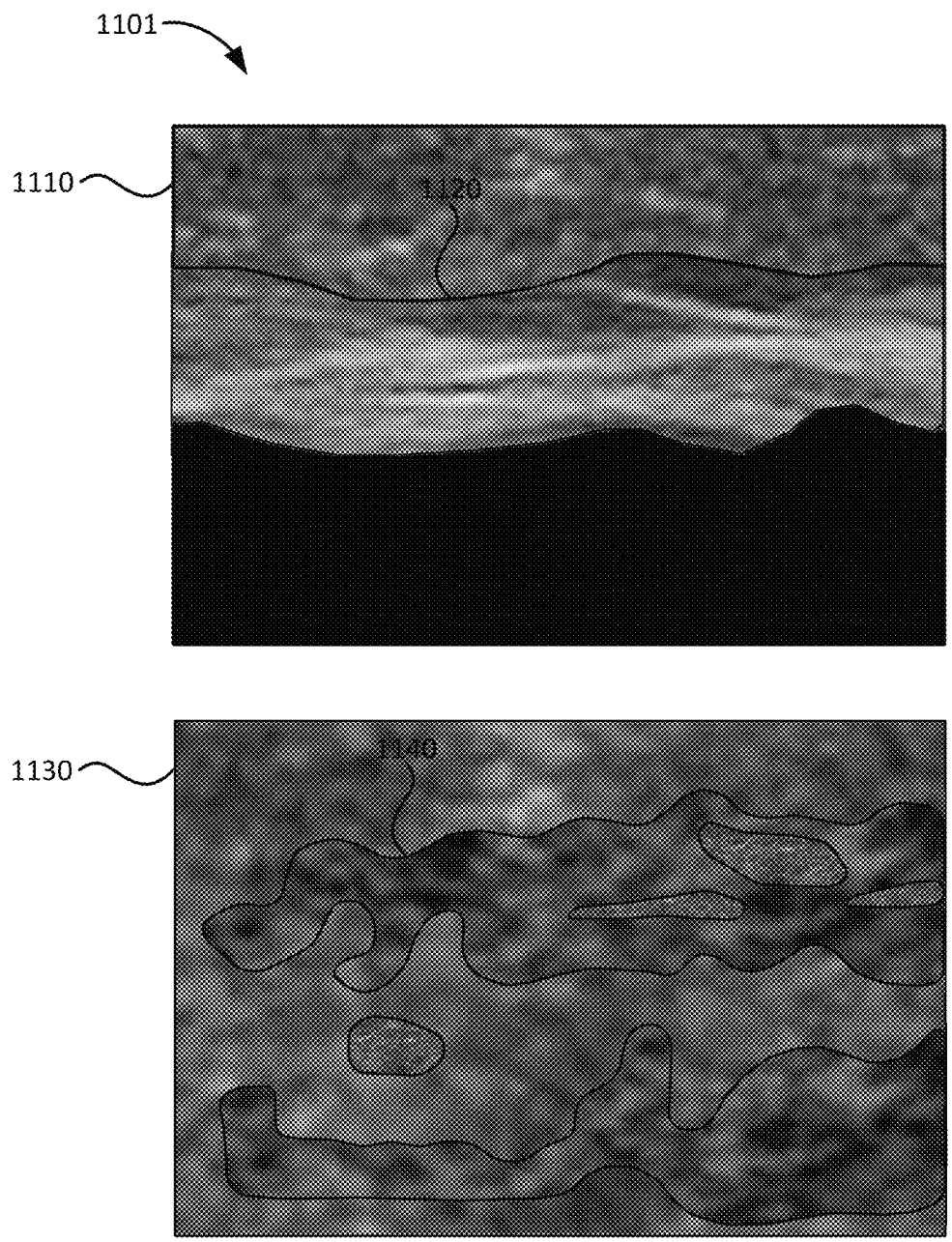
FIG. 11 is a diagram illustrating the use of elastography for implant assessment according to an implementation described herein.

FIG. 11 is a diagram 1101 illustrating the use of elastography in assessing a breast implant. As shown in FIG. 11, an ultrasound image 1110 may undergo segmentation to identify the boundaries of implant capsule 1120. Similarly, an elastography image 1120 may undergo segmentation to identify areas with different values of stiffness. For example, a segmented area 1140 in elastography image 1130 may provide different information than the segmented implant capsule 1120 in an ultrasound image. Thus, ultrasound ML model 644 may be trained to perform segmentation to identify areas associated with a particular tissue stiffness and/or to identify particular a particular pathology associated with a particular tissue stiffness.

Figure 12A:
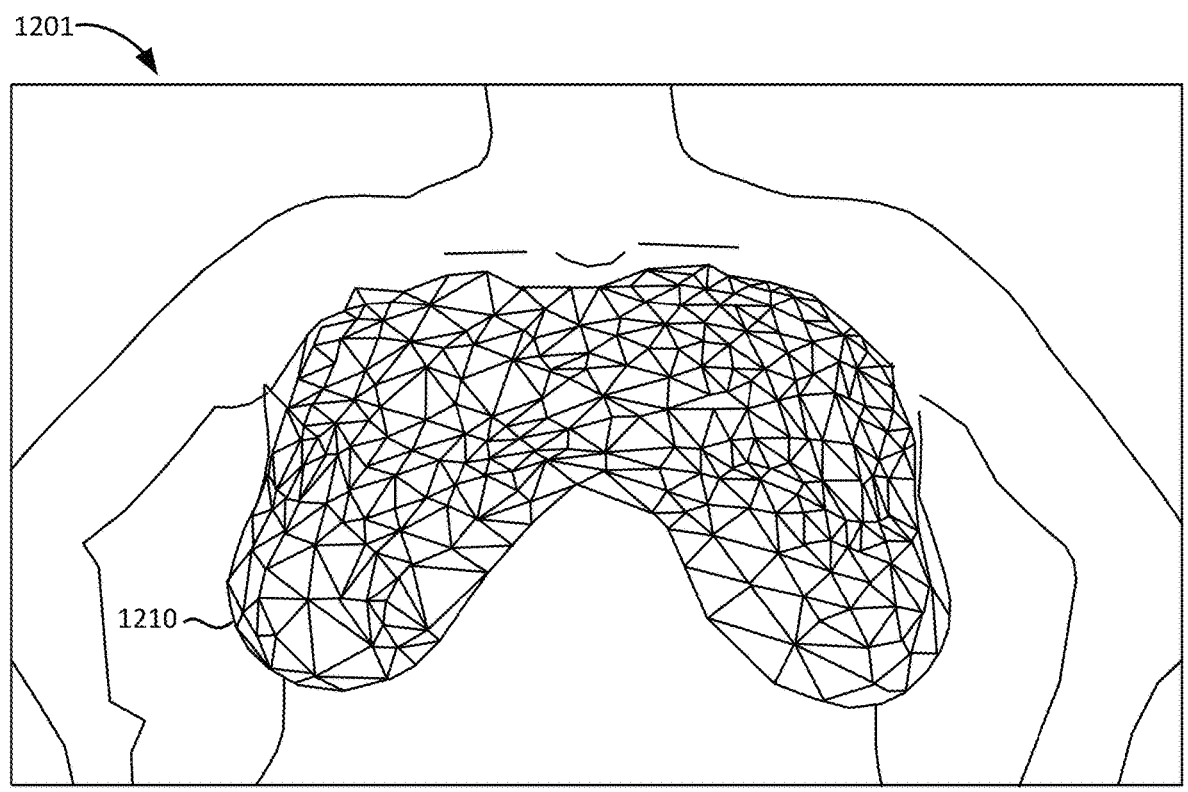
FIG. 12A is a diagram illustrating the use of a three-dimensional (3D) mesh on a depth camera image according to an implementation described herein.

FIG. 12A is a diagram 1201 illustrating the use of a 3D triangular mesh on a 3D scan image. As shown in FIG. 12A, one or more optical images captured using depth camera 230 may be processed to remove backgrounds and converted into a point cloud or a 3D triangular mesh 1210 that covers the patient's breast area. If the depth data in the captures optical images includes noise that is above a particular threshold, noise reduction techniques may be applied to the data to improve the accuracy of the point cloud.

Figure 12B:
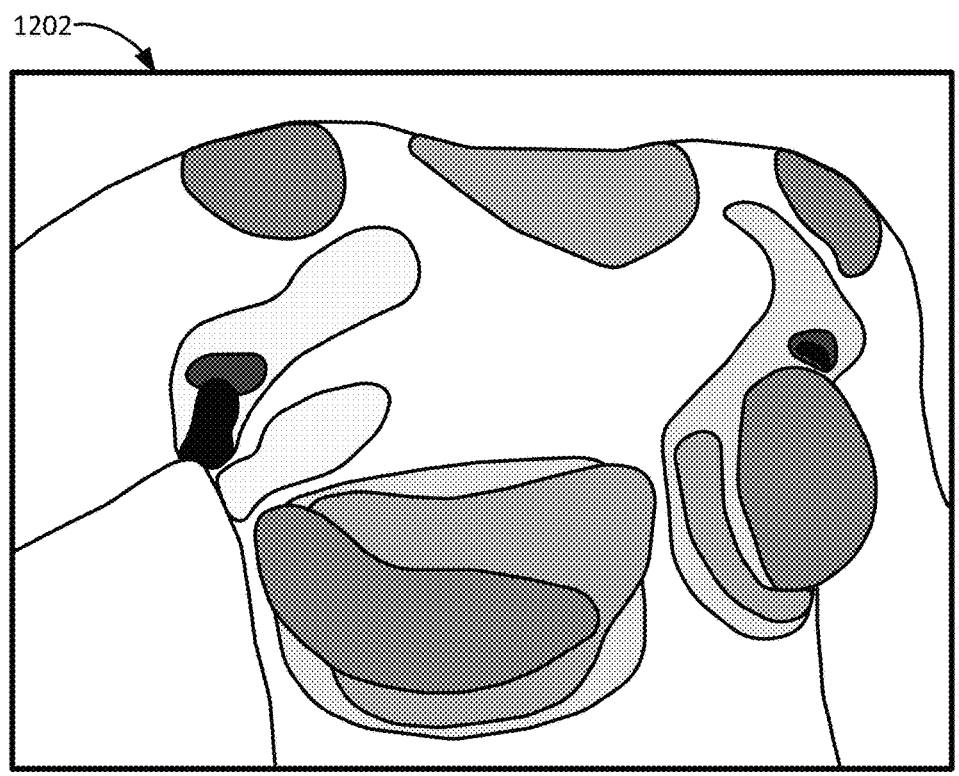
FIG. 12B is a diagram illustrating a curvature plot on a depth camera image according to an implementation described herein.

FIG. 12B is a diagram 1202 illustrating a 3D geometrical feature plot where the 3D geometrical feature corresponds to curvature. As shown in FIG. 12B, diagram 1202 illustrates a generated 3D curvature plot. 3D curvature plot may display areas associated with a particular range of curvature values with a particular shading, color, or pattern. The 3D curvature plot may be used to identify a change in the morphology or integrity of a patient's breast and/or breast implant. For example, the 3D curvature plot may be used to perform a symmetry analysis to determine whether the left and right breasts are within a particular symmetry threshold. Furthermore, a baseline and follow-up 3D curvature plot may be used to visually assess a change in the shape of the patient's breast area.

The 3D curvature plot may be used to calculate one or more values for the patient's breast area, such as, for example, the size and/or volume of a breast, the angle of a breast with respect to the patient's rib cage, the distance between a point on a breast and a reference point on the patient's rib cage, and/or another measurement value. Moreover, depth camera 230 may be used to obtain 3D scan images in different postures, such as while the patient is supine, incline, upright, standing, etc. 3D curvature plots associated with different postures may be used to track the change in the shape of the patient's breasts in different postures to generate additional information relating to the morphology or integrity of the patient's breast and/or breast implant.

Furthermore, the generated point cloud and/or 3D triangular mesh, and/or the generated 3D curvature plot may be used as an input into a trained machine learning model, such as breast morphology ML model 650. For example, breast morphology ML model 650 may be trained to detect, based on an input of a 3D curvature plot, an area in the 3D curvature plot that has experienced contracture, an area in the 3D curvature plot that has experienced a rupture, and/or an area in the 3D curvature plot that has experienced another type of abnormality.

Figure 13A:
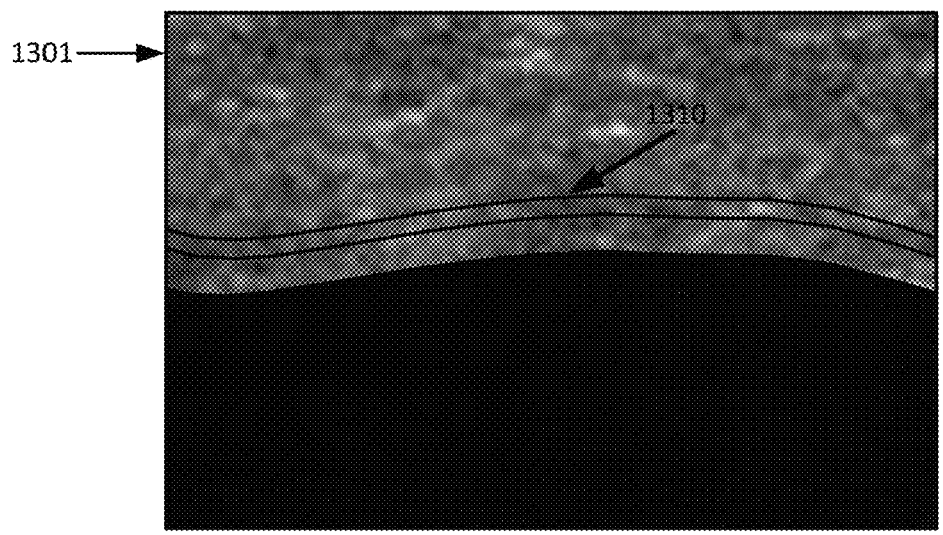
FIGS. 13A, 13B, and 13C are diagrams illustrating segmented ultrasound scans of an implant capsule according to an implementation described herein.
Figure 13B:
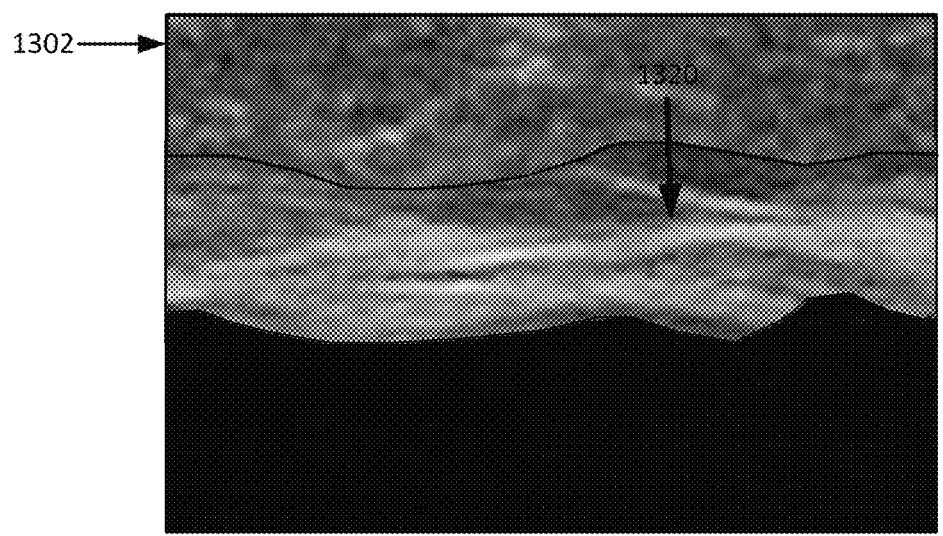
Figure 13C:
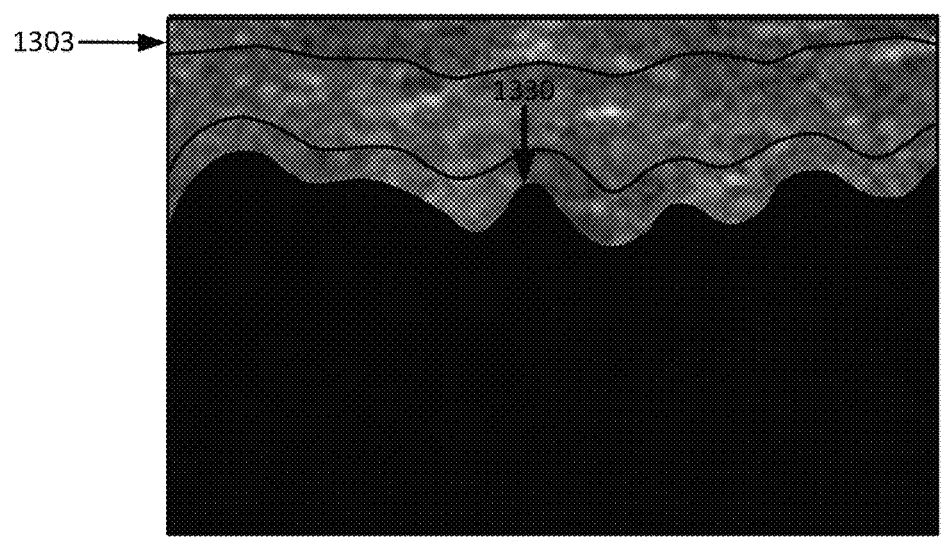

FIG. 13A illustrates a segmented ultrasound image 1301 that includes a normal implant capsule 1310. As shown in FIG. 13A, normal implant capsule 1310 may include clearly delineated and smooth boundaries and may not exhibit any thickening due to fibrous tissue or radial folds. FIG. 13B illustrates a segmented ultrasound image 1302 that includes a thickened implant capsule 1320 with excessive fibrous tissue as a result of capsular contracture. FIG. 13C illustrates a segmented ultrasound image 1303 that includes radial folds 1330 in the implant capsule, giving the implant capsule a wavy appearance. Radial folds 1330 in an implant capsule may be caused by capsular contracture of the implant.

Figure 14A:
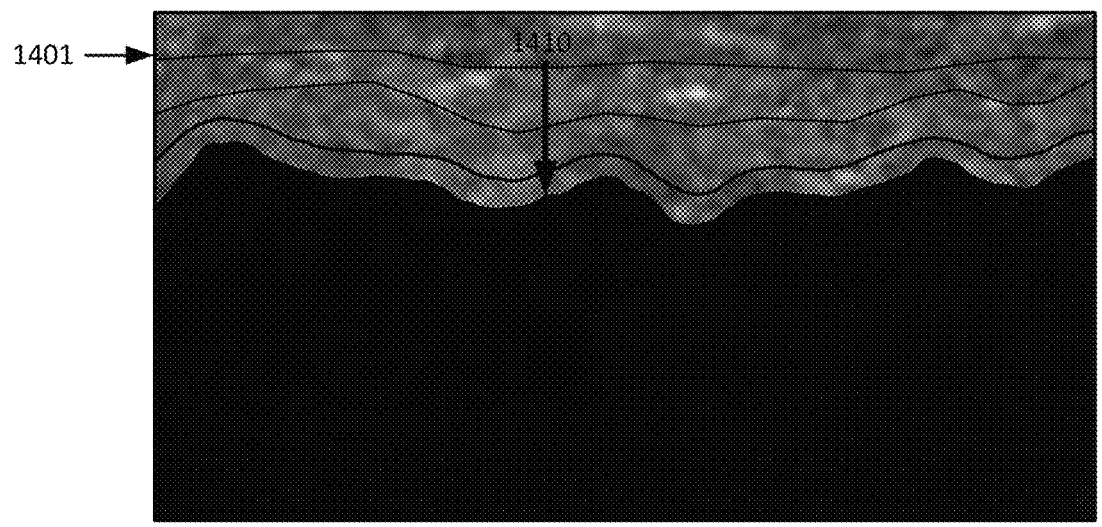
FIGS. 14A, 14B, and 14C are diagrams illustrating the characterization of an implant capsule according to an implementation described herein.
Figure 14B:
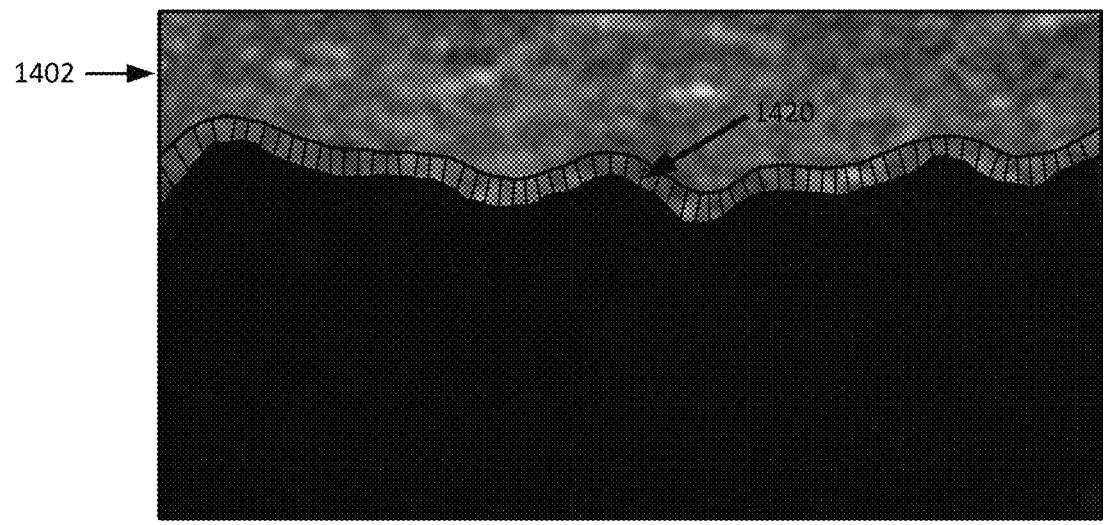

FIG. 14A illustrates an ultrasound image 1401 that includes a segmented implant capsule 1410. For example, implant capsule ML model 650 may be trained to perform segmentation to identify the boundaries of an implant capsule. FIG. 14B illustrates an ultrasound image 1402 that includes computed thickness values 1420 determined based on the segmented implant capsule 1410. For example, implant capsule ML model 650 may be trained to calculate the thickness of the implant capsule based on the distance between the boundaries of the implant capsule identified by the segmentation.

Figure 14C:
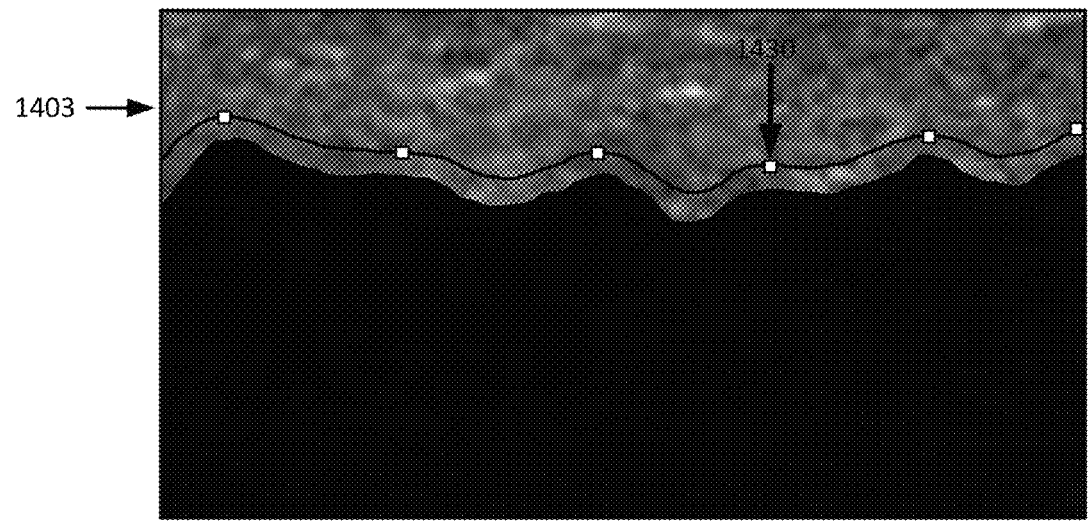

FIG. 14C illustrates an ultrasound image 1403 that includes identified radial folds 1430. For example, implant capsule ML model 650 may be trained to identify radial fold points based on the segmented implant capsule 1410. The determined thickness of the implant capsule and/or the determined radial fold count for the implant capsule may be used to determine whether the implant capsule is associated with capsular contracture and/or an extent of the capsular contracture, such as the Baker class associated with the capsular contracture.

Figure 15:
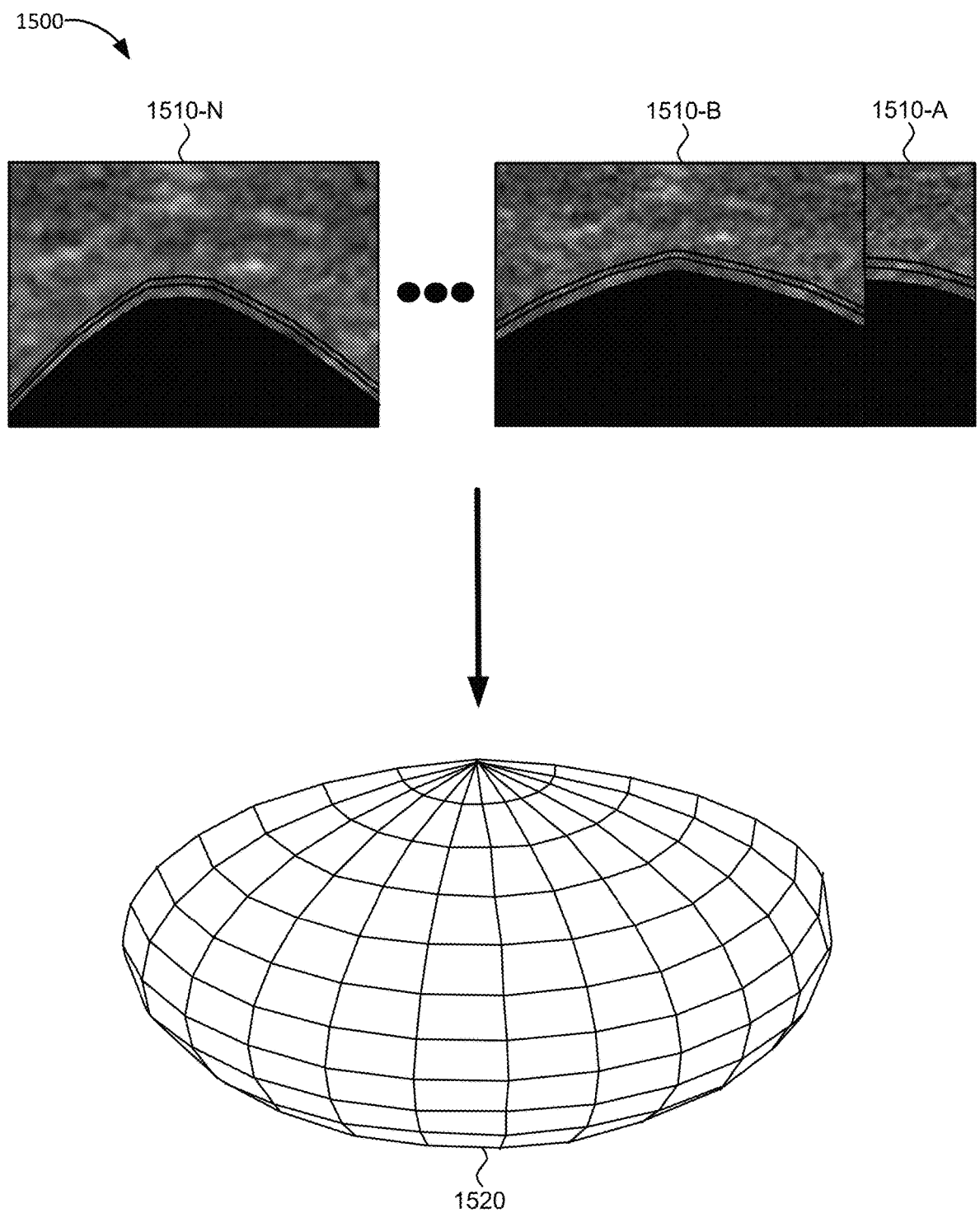
FIG. 15 is a diagram illustrating generation of a 3D shape from a series of segmented ultrasound images according to an implementation described herein.

FIG. 15 is a diagram illustrating generation of a 3D shape 1520 from a series of segmented ultrasound images 1510-A to 1510-N. As shown in FIG. 15, each ultrasound image 1510 may correspond to a different slice through the implant, enabling the stitching together or connecting of the segmented boundary from each ultrasound image 1510 to generate 3D shape 1520 of an implant capsule.

Figure 16A:
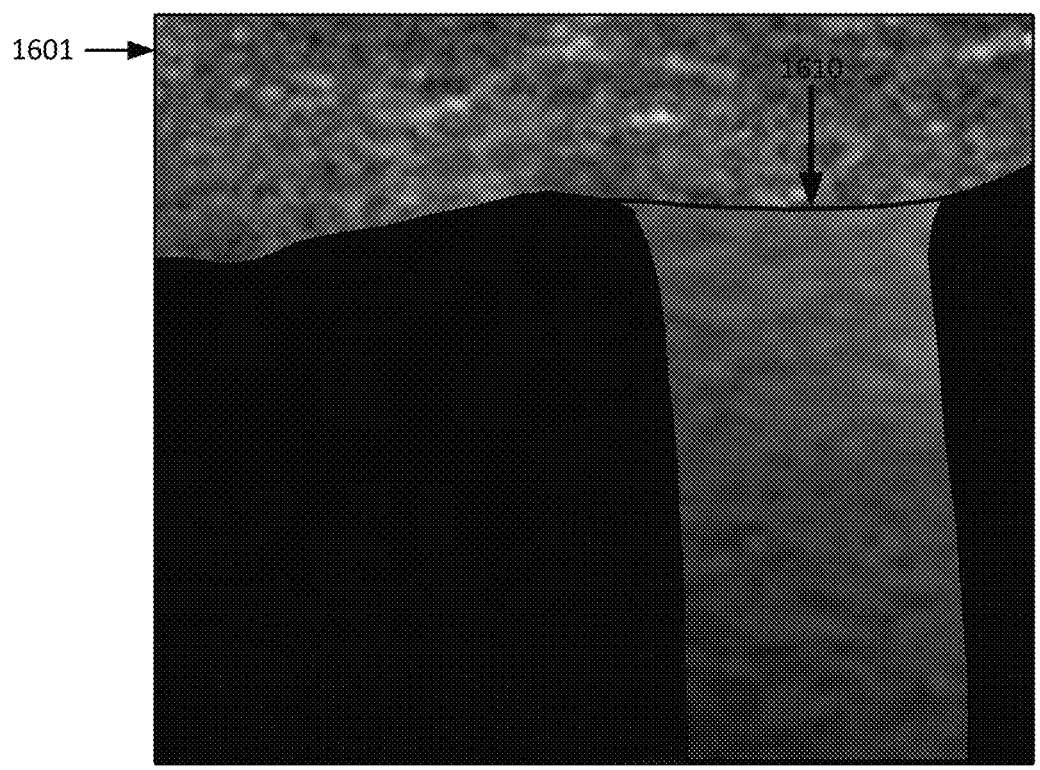
FIGS. 16A and 16B are diagrams illustrating the characterization of capsule ruptures according to an implementation described herein.
Figure 16B:
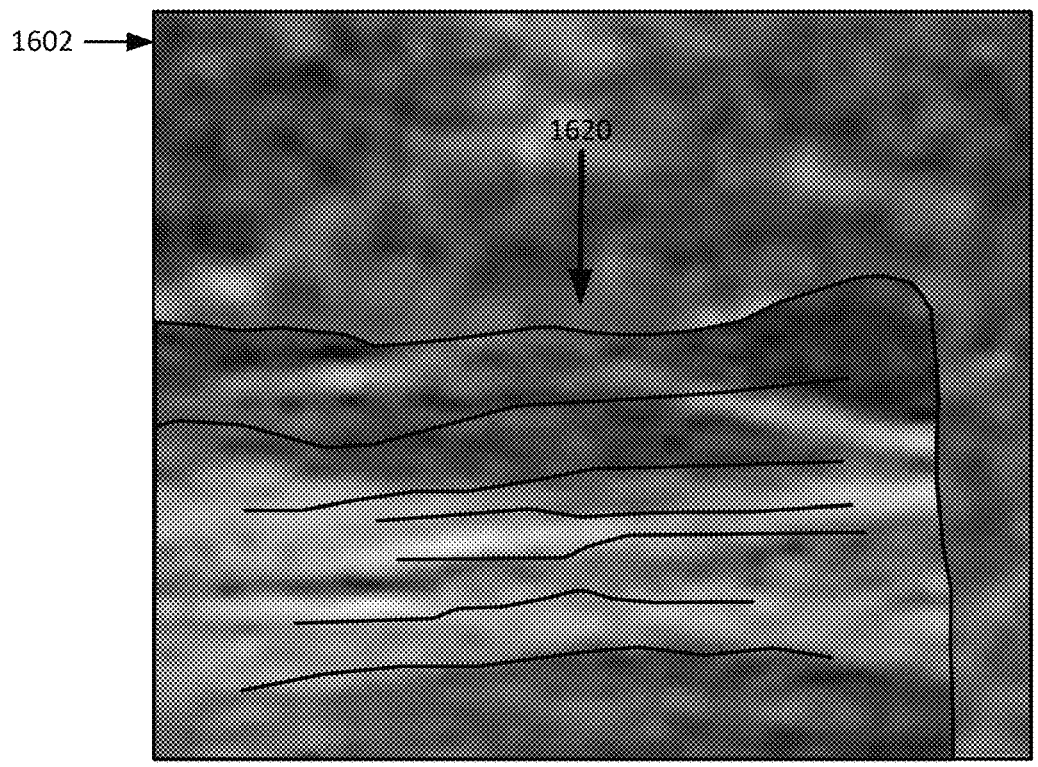

FIG. 16A illustrates a segmented ultrasound image 1601 that includes an identified extracapsular rupture 1610. For example, ultrasound ML model 644 may be trained to identify an extracapsular rupture in an ultrasound image and to perform segmentation to identify the borders of extracapsular rupture 1610. Extracapsular rupture 1610 may be used to generate a medical intervention recommendation, such as, for example, to recommend the patient for an implant replacement. FIG. 16B illustrates a segmented ultrasound image 1602 that includes an identified intracapsular rupture 1620. For example, ultrasound ML model 644 may be trained to identify an intracapsular rupture in an ultrasound image and to perform segmentation to identify the borders of intracapsular rupture 1620. Intracapsular rupture 1620 may be used to generate a medical intervention recommendation, such as, for example, to recommend the patient for an implant replacement. Ultrasound ML model 644 may be trained to identify other types of specific features, such as, for example, a diffuse snowstorm sign in an ultrasound image. A diffuse snowstorm sign may indicate extracapsular rupture and may be used to generate a medical intervention recommendation, such as, for example, to recommend the patient for an implant replacement.

Figure 17A:
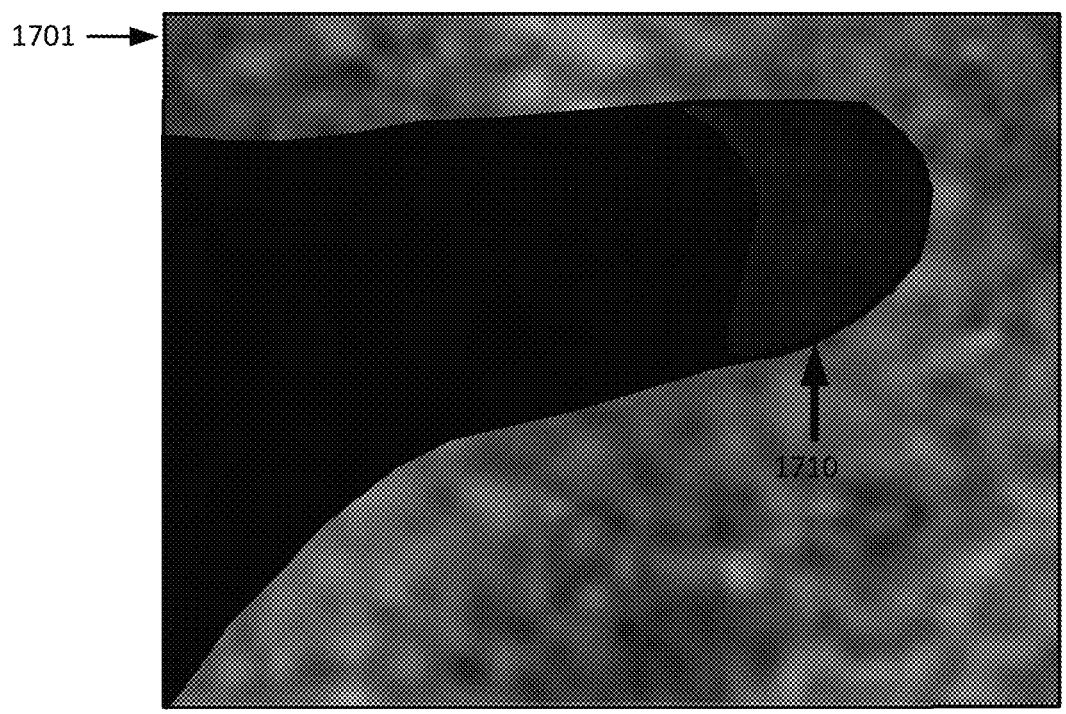
FIGS. 17A and 17B are diagrams illustrating the characterization of fluid collections according to an implementation described herein.
Figure 17B:
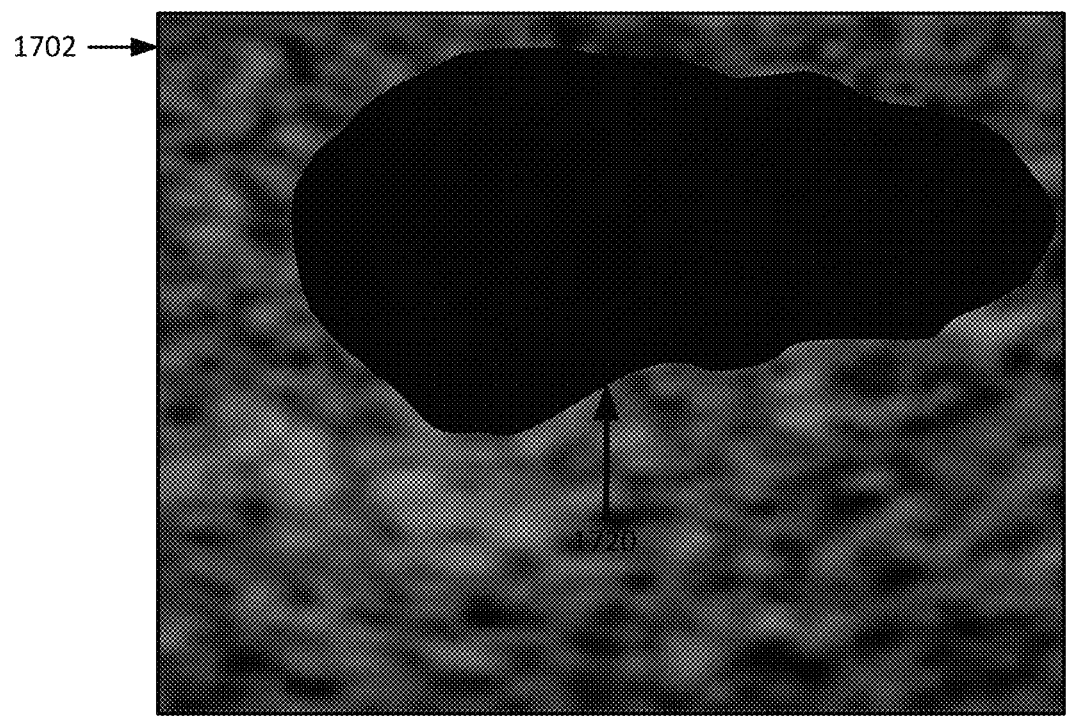

FIGS. 17A and 17B illustrate segmentation to identify fluid collections. FIG. 17A illustrates a segmented ultrasound image 1701 that includes an identified peri-implant hematoma 1710. For example, ultrasound ML model 644 may be trained to identify a hematoma in an ultrasound image and to perform segmentation to identify the borders of hematoma 1710. Hematoma 1710 may be used to help with an implant assessment by a medical professional. FIG. 17B illustrates an ultrasound image 1702 that includes an identified breast abscess 1720. For example, ultrasound ML model 644 may be trained to identify a breast abscess in an ultrasound image and to perform segmentation to identify the borders of breast abscess 1720. Breast abscess 1720 may be used to help with an implant assessment by a medical professional.

Figure 18A:
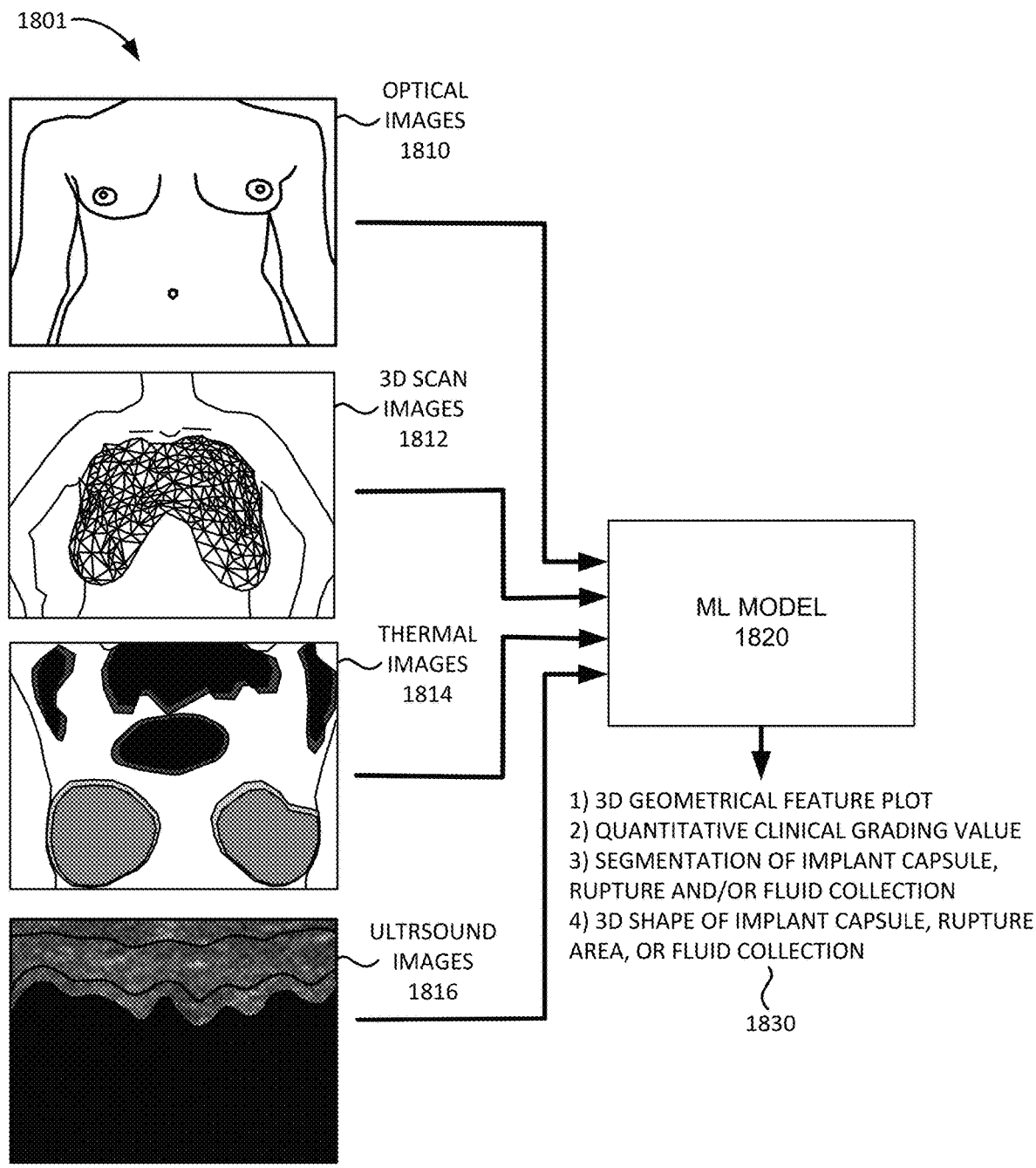
FIGS. 18A and 18B are diagrams illustrating exemplary machine learning models according to an implementation described herein.

FIG. 18A is a diagram 1801 illustrating a first exemplary ML model according to an implementation described herein. As shown in FIG. 18A, optical images 1810, 3D scan images 1812, thermal camera images 1814, and ultrasound images 1816 may be provided as input into trained ML model 1820. For example, trained ML model 1820 may include optical ML model 614, 3D scan ML model 624, thermal ML model 634, and/or ultrasound ML model 644. Trained ML model 1820 may be trained to generate output 1830 that includes one or more of a 3D geometrical feature plot based on the inputted images; to classify the inputted images into a particular quantitative clinical grading value; to perform a segmentation of an implant capsule, a rupture area and/or a fluid collection; and/or to generate a 3D shape of an implant capsule, rupture area and/or fluid collection based on the segmentation. In other implementation, multiple ML models may be trained to generate these different types of classification and/or feature extraction outputs.

Figure 18B:
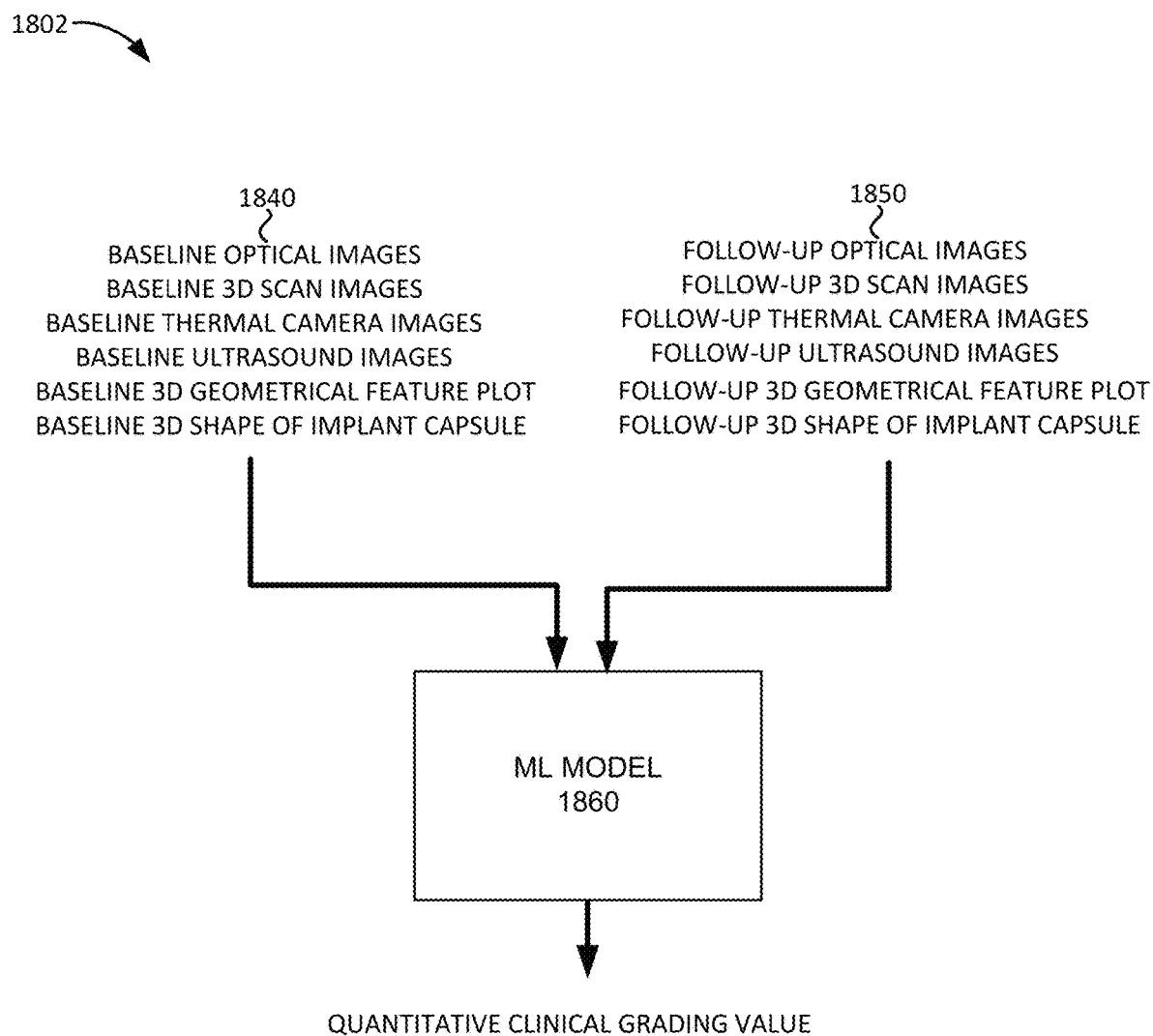

FIG. 18B is a diagram 1802 illustrating a second exemplary ML model according to an implementation described herein. As shown in FIG. 18B, input 1840 may include baseline optical images, baseline 3D scan images, baseline thermal camera images, and/or baseline ultrasound images. Additionally, input 1840 may include a baseline 3D geometrical feature plot and/or a baseline 3D shape of the implant capsule generated by another ML model.

Input 1850 may include follow-up optical images, follow-up 3D scan images, follow-up thermal camera images, and/or follow-up ultrasound images. Additionally, input 1850 may also include a follow-up 3D geometrical feature plot and/or a follow-up 3D shape of the implant capsule generated by the other ML model. ML model 1860 may be trained to take inputs 1840 and 1850 and to classify the inputs into a particular quantitative clinical grading value, such as, for example, a Baker class value, an implant capsule thickness value, a radial fold count value, an implant capsule smoothness value, and/or another type of quantitative clinical grading value.

Figure 19A:
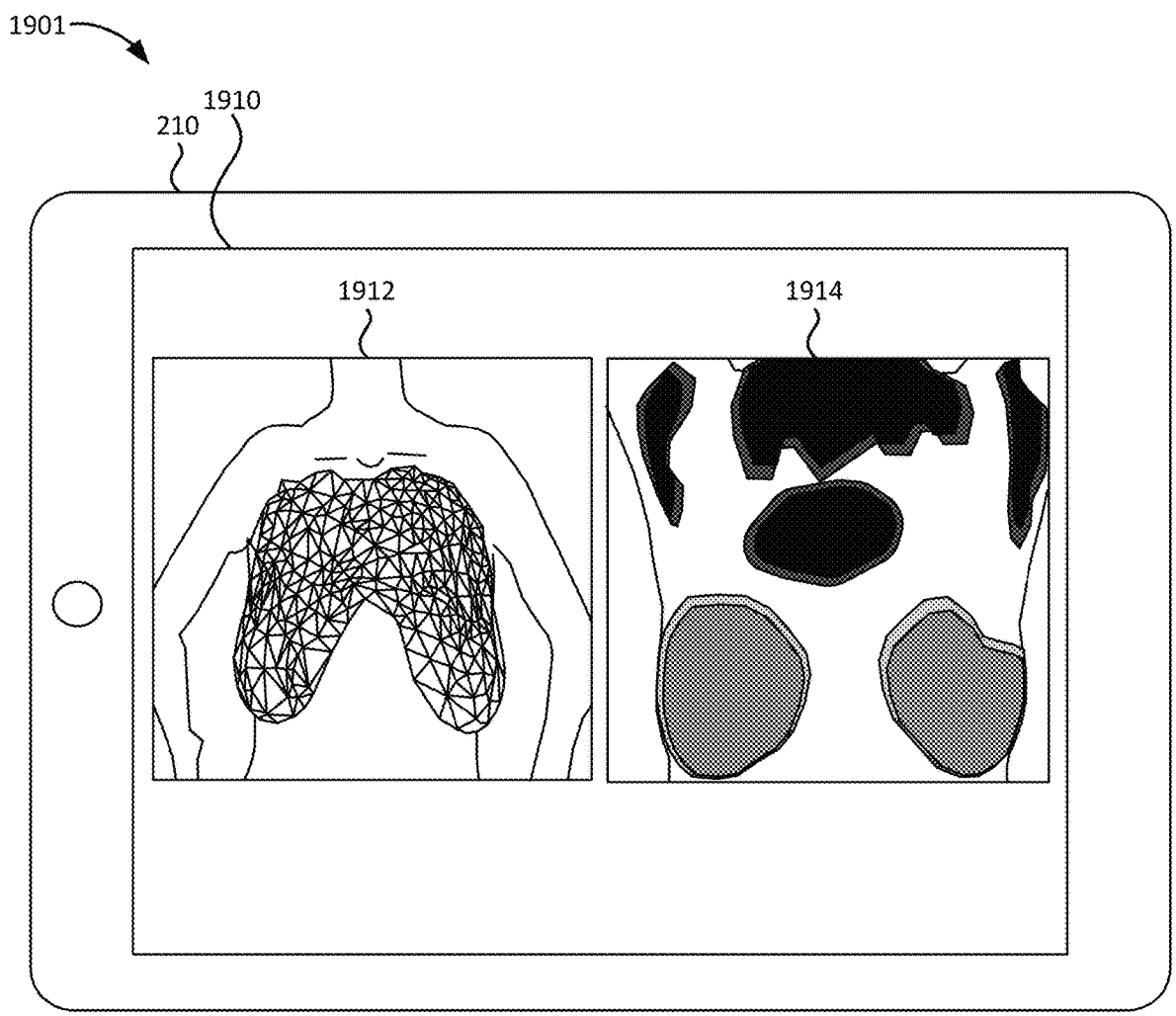
FIG. 19A is a diagram illustrating a first exemplary user interface according to an implementation described herein.

FIG. 19A is a diagram illustrating an exemplary user interface 1901 according to an implementation described herein. As shown in FIG. 19A, controller unit 210 may generate a display 1910 that includes different types of images side by side. For example, display 1910 may display a 3D mesh image 1912 next to a thermal camera image 1914. The images may be displayed in real-time or near real-time. Controller unit 210 may display any combination of types of images, such as an ultrasound image next to an optical image, an ultrasound image next to a 3D scan image, an ultrasound image next to a thermal camera image, an optical image next to a 3D scan image, an optical image next to a thermal camera image, and/or a 3D scan image next to a thermal camera image. A user may select which types of images to display on display 1910.

Figure 19B:
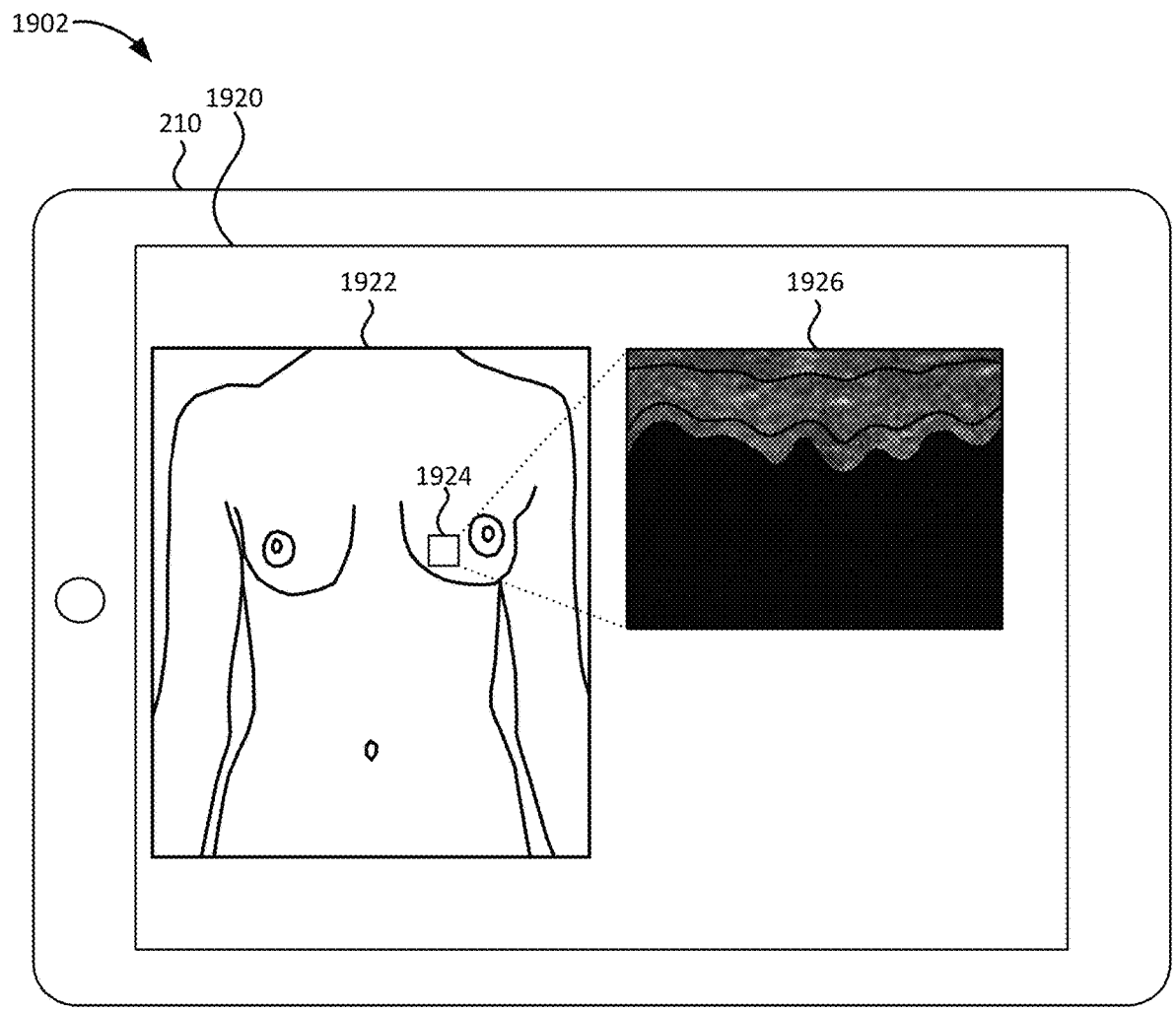
FIG. 19B is a diagram illustrating a second exemplary user interface according to an implementation described herein.

FIG. 19B is a diagram illustrating an exemplary user interface 1902 according to an implementation described herein. As shown in FIG. 19B, controller unit 210 may generate a display 1920 that includes a first type of image with an ultrasound image and an indication of a location on the first type of image corresponding to the ultrasound image. For example, display 1920 may display an optical image 1922 of a patient's breast area and an indication 1924 that corresponds to the location on the patient's breast area associated with a displayed ultrasound image 1926. The user may select different areas on optical image 1922 to display ultrasound images associated with a selected area. Furthermore, controller unit 210 may display, on optical image 1922, indications associated with areas where particular abnormalities have been detected.

Figure 19C:
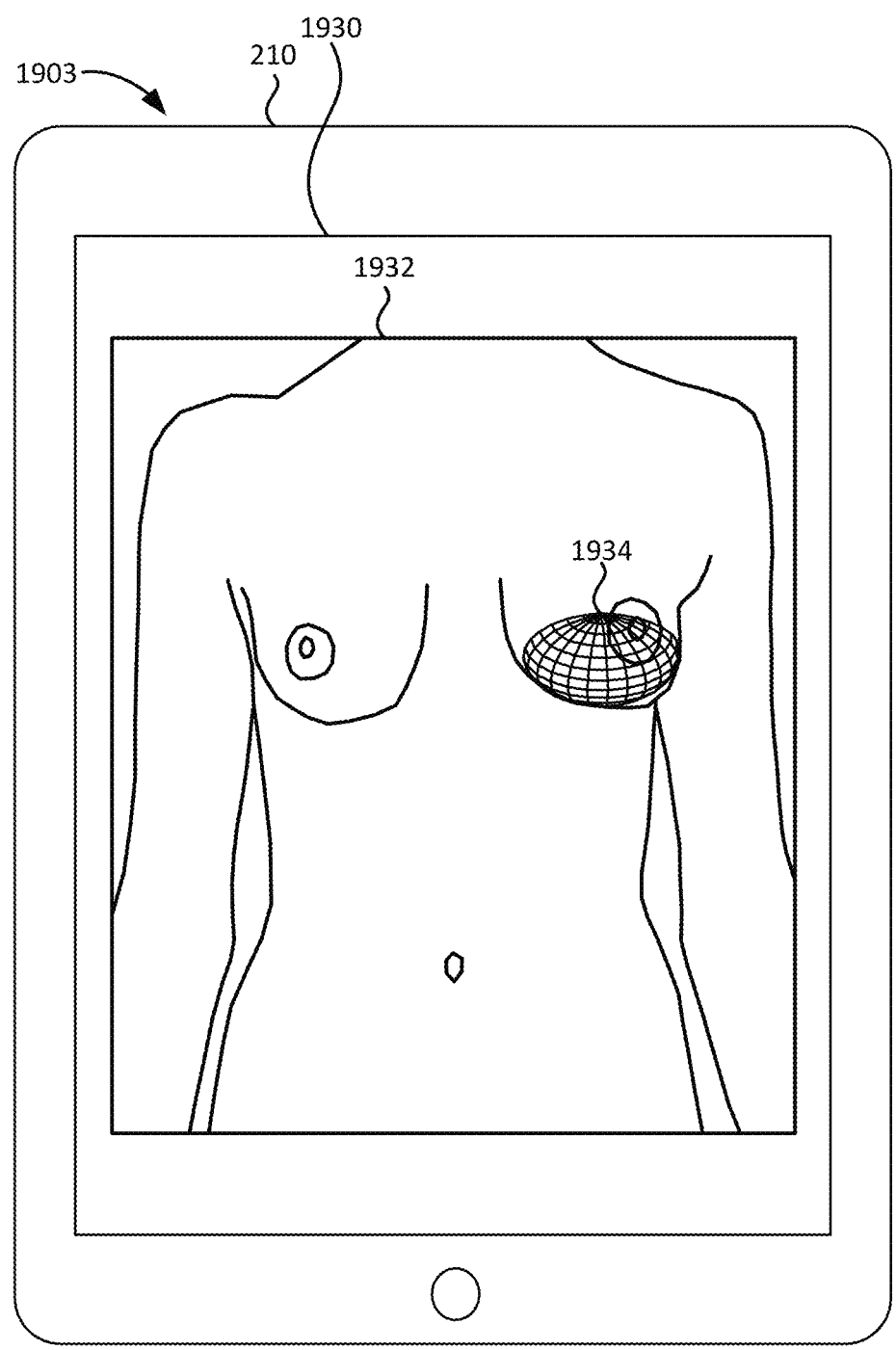
FIG. 19C is a diagram illustrating a third exemplary user interface according to an implementation described herein.

FIG. 19C is a diagram illustrating an exemplary user interface 1903 according to an implementation described herein. As shown in FIG. 19C, controller unit 210 may generate a display 1930 that includes a first type of image with an overlay of a generated 3D shape. For example, display 1930 may display an optical image 1932 with an overlaid generated 3D shape 1934 that was generated from a series of ultrasound images segmented to identify the boundaries of an implant capsule. In the preceding specification, various preferred embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

For example, while a series of blocks have been described with respect to FIGS. 7, 8, and 9, the order of the blocks may be modified in other implementations. Further, non-dependent blocks may be performed in parallel.

It will be apparent that systems and/or methods, as described above, may be implemented in many different forms of software, firmware, and hardware in the implementations illustrated in the figures. The actual software code or specialized control hardware used to implement these systems and methods is not limiting of the embodiments. Thus, the operation and behavior of the systems and methods were described without reference to the specific software code—it being understood that software and control hardware can be designed to implement the systems and methods based on the description herein.

Further, certain portions, described above, may be implemented as a component that performs one or more functions. A component, as used herein, may include hardware, such as a processor, an ASIC, or a FPGA, or a combination of hardware and software (e.g., a processor executing software).

It should be emphasized that the terms "comprises"/"comprising" when used in this specification are taken to specify the presence of stated features, integers, steps or components but does not preclude the presence or addition of one or more other features, integers, steps, components or groups thereof.

The term "logic," as used herein, may refer to a combination of one or more processors configured to execute instructions stored in one or more memory devices, may refer to hardwired circuitry, and/or may refer to a combination thereof. Furthermore, a logic may be included in a single device or may be distributed across multiple, and possibly remote, devices.

For the purposes of describing and defining the present invention, it is additionally noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

No element, act, or instruction used in the present application should be construed as critical or essential to the embodiments unless explicitly described as such. Also, as used herein, the article "a" is intended to include one or more items. Further, the phrase "based on" is intended to mean "based, at least in part, on" unless explicitly stated otherwise.

What is claimed is:

1. A method performed by a computing device, the method comprising:
  obtaining, by the computing device, a baseline ultrasound image of a patient's breast area, wherein the baseline ultrasound image was obtained during an initial patient visit;
  obtaining, by the computing device, a follow-up ultrasound image of the patient's breast area, wherein the follow-up ultrasound image was obtained during a follow-up patient visit;
  using, by the computing device, one or more machine learning models to compare the baseline ultrasound image with the follow-up ultrasound image by using the baseline ultrasound image and the follow-up ultrasound image as inputs into the one or more machine learning models;

detecting, by the computing device, a change in a morphology or integrity of an implant, or tissues surrounding the implant, in the patient's breast area based on the comparison of the baseline ultrasound image with the follow-up ultrasound image; and generating, by the computing device, a recommendation for a medical intervention based on the detected change.

2. The method of claim 1, further comprising:

obtaining a baseline optical image of the patient's breast area;

obtaining a follow-up optical image of the patient's breast area;

using the one or more machine learning models to compare the baseline optical image with the follow-up optical image; and wherein detecting the change in the morphology or integrity of the implant, or the tissues surrounding the implant, in the patient's breast area is further based on the comparison of the baseline optical image with the follow-up optical image.

3. The method of claim 1, further comprising:

obtaining a baseline three-dimensional (3D) scan image of the patient's breast area;

obtaining a follow-up 3D scan image of the patient's breast area;

using the one or more machine learning models to compare the baseline 3D scan image with the follow-up 3D scan image; and wherein detecting the change in the morphology or integrity of the implant, or the tissues surrounding the implant, in the patient's breast area is further based on the comparison of the baseline 3D scan image with the follow-up 3D scan image.

4. The method of claim 1, further comprising:

obtaining a baseline thermal camera image of the patient's breast area;

obtaining a follow-up thermal camera image of the patient's breast area;

using the one or more machine learning models to compare the baseline thermal camera image with the follow-up thermal camera image; and detecting a change in a morphology, integrity or temperature variation of the patient's breast area based on the comparison of the baseline thermal camera image with the follow-up thermal camera image.

5. The method of claim 1, further comprising:

obtaining a baseline elastography image of the patient's breast area;

obtaining a follow-up elastography image of the patient's breast area;

using the one or more machine learning models to compare the baseline elastography image with the follow-up elastography image; and detecting a change in a morphology, integrity, or stiffness of the patient's breast area based on the comparison of the baseline elastography image with the follow-up elastography image.

6. The method of claim 3, further comprising:

obtaining a three-dimensional (3D) scan image of the patient's breast area using one or more depth cameras;

generating a 3D geometrical feature plot using the obtained 3D scan image; and using the generated 3D geometrical feature plot as an input into the one or more machine learning models.

7. The method of claim 1, wherein using the one or more machine learning models to compare the baseline ultrasound image with the follow-up ultrasound image includes:

using the one or more machine learning models to determine a quantitative clinical grading value for the morphology or integrity of the patient's breast area.

8. The method of claim 1, further comprising:

using the one or more machine learning models to perform a segmentation of an implant capsule, a rupture area, or a fluid collection associated with the implant in an ultrasound image of the patient's breast area.

9. The method of claim 8, further comprising:

using a plurality of ultrasound images that include the segmentation of the implant capsule, the rupture area, or the fluid collection associated with the implant to generate a three-dimensional (3D) shape of the implant capsule, the rupture area, or the fluid collection.

10. The method of claim 1, further comprising:

using the one or more machine learning models to determine whether the implant in the patient's breast area is associated with at least one of:

an extracapsular rupture, an intracapsular rupture, a capsular contracture, or a fluid collection.

11. The method of claim 1, wherein obtaining the baseline ultrasound image of the patient's breast area and obtaining the follow-up ultrasound image of the patient's breast area include:

dividing the breast area into a plurality of sectors;

scanning particular ones of the plurality of sectors using an ultrasound probe;

indicating, on a user interface, which ones of the plurality of sectors has been scanned;

receiving, via the user interface, a selection of a scanned sector of the plurality of sectors; and displaying, in the user interface, one or more ultrasound images associated with the selected scanned sector.

12. The method of claim 1, wherein at least one of the baseline ultrasound image and follow-up ultrasound image includes a B-mode ultrasound image, a Power Doppler ultrasound image, a Continuous Wave Doppler ultrasound image, a Pulsed Wave Doppler ultrasound image, a Probability Mode ultrasound image, or a motion mode ultrasound image.

13. A system comprising:

an ultrasound probe; and a controller unit configured to:

obtain a baseline ultrasound image of a patient's breast area using the ultrasound probe, wherein the baseline ultrasound image was obtained during a first patient visit;

obtain a follow-up ultrasound image of the patient's breast area using the ultrasound probe, wherein the follow-up ultrasound image was obtained during a later patient visit;

use one or more machine learning models to compare the baseline ultrasound image with the follow-up ultrasound image by using the baseline ultrasound image and the follow-up ultrasound image as inputs into the one or more machine learning models;

detect a change in a morphology or integrity of an implant, or tissues surrounding the implant, in the patient's breast area based on the comparison of the baseline ultrasound image with the follow-up ultrasound image; and generate a recommendation for a medical intervention based on the detected change.

14. The system of claim 13, further comprising:
a depth camera; and
wherein the controller unit is further configured to:
  obtain a baseline optical or three-dimensional (3D) scan image of the patient's breast area using the depth camera;
  obtain a follow-up optical or 3D scan image of the patient's breast area using the depth camera;
  use the one or more machine learning models to compare the baseline optical or 3D scan image with the follow-up optical or 3D scan image; and
  wherein the controller unit is further configured to detect the change in the morphology or integrity of the implant, or the tissues surrounding the implant, in the patient's breast area based on the comparison of the baseline optical or 3D scan image with the follow-up optical or 3D scan image.

15. The system of claim 14, wherein the controller unit is further configured to:
  obtain a 3D scan image of the patient's breast area using the depth camera;
  generate a 3D geometrical feature plot using the obtained 3D scan image; and
  use the generated 3D geometrical feature plot as an input into the one or more machine learning models.

16. The system of claim 13, wherein the controller unit is further configured to:
  obtain a baseline elastography image of the patient's breast area using the ultrasound probe;
  obtain a follow-up elastography image of the patient's breast area using the ultrasound probe;
  use the one or more machine learning models to compare the baseline elastography image with the follow-up elastography image; and
  wherein the controller unit is further configured to detect the change in the morphology or integrity of the implant, or the tissues surrounding the implant, in the patient's breast area based on the comparison of the baseline elastography image with the follow-up elastography image.

17. The system of claim 13, wherein, when using the one or more machine learning models to compare the baseline ultrasound image with the follow-up ultrasound image, the controller unit is further configured to:
  use the one or more machine learning models to determine a quantitative clinical grading value for the morphology or integrity of the patient's breast area.

18. The system of claim 13, wherein the controller unit is further configured to:
  use the one or more machine learning models to perform a segmentation of an implant capsule, a rupture area, or a fluid collection in an ultrasound image of the patient's breast area; and
  use a plurality of ultrasound images that include the segmentation of the implant capsule, the rupture area, or the fluid collection associated with the implant to generate a three-dimensional (3D) shape of the implant capsule, the rupture area, or the fluid collection.

19. The system of claim 13, wherein the controller unit is further configured to:

use the one or more machine learning models to determine whether the implant in the patient's breast area is associated with at least one of:
  an extracapsular rupture,
  an intracapsular rupture,
  capsular contracture, or
  a fluid collection.

20. A device comprising:
logic configured to:
  obtain a baseline ultrasound image of a patient's breast area using an ultrasound probe, wherein the baseline ultrasound image was obtained during an initial patient visit;
  obtain a follow-up ultrasound image of the patient's breast area using the ultrasound probe, wherein the follow-up ultrasound image was obtained during a follow-up patient visit;
  obtain a baseline optical or three-dimensional (3D) scan image of the patient's breast area using a depth camera;
  obtain a follow-up optical or 3D scan image of the patient's breast area using the depth camera;
  use one or more machine learning models to compare the baseline ultrasound image with the follow-up ultrasound image and the baseline optical or 3D scan image with the follow-up optical or 3D scan image by using the baseline ultrasound image, the follow-up ultrasound image, the baseline optical or 3D scan image, and the follow-up optical or 3D scan image as inputs into the one or more machine learning models;
  detect a change in a morphology or integrity of an implant, or tissues surrounding the implant, in the patient's breast area based on the comparison of the baseline ultrasound image with the follow-up ultrasound image and the comparison of the baseline optical or 3D scan image with the follow-up optical or 3D scan image; and
  generate a recommendation for a medical intervention based on the detected change.

21. A method performed by a computing device, the method comprising:
  obtaining, by the computing device, an ultrasound image of a patient's breast area;
  obtaining, by the computer device, at least one of an optical image of the patient's breast area, a three-dimensional (3D) scan image of the patient's breast area obtained using a depth camera, or a thermal camera image of the patient's breast area;
  using, by the computing device, one or more machine learning models to compare the ultrasound image with the at least one of the optical image of the patient's breast area, the 3D scan image of the patient's breast area, or the thermal camera image of the patient's breast area by using the ultrasound image and the at least one of the optical image of the patient's breast area, the 3D scan image of the patient's breast area, or the thermal camera image of the patient's breast area as inputs into the one or more machine learning models;
  detecting, by the computing device, a change in a morphology or integrity of an implant, or tissues surrounding the implant, in the patient's breast area based on the comparison; and
  generating, by the computing device, a recommendation for a medical intervention based on the detected change.

* * * * *